(12) United States Patent
Lee-Sepsick

(10) Patent No.: US 12,156,641 B2
(45) Date of Patent: Dec. 3, 2024

(54) METHODS AND COMPOSITIONS FOR ENDOMETRIAL CELL AND TISSUE SAMPLING

(71) Applicant: FEMASYS INC., Suwanee, GA (US)

(72) Inventor: Kathy Lee-Sepsick, Suwanee, GA (US)

(73) Assignee: Femasys Inc., Suwanee, GA (US)

( * ) Notice: Subject to any disclaimer, the term of this patent is extended or adjusted under 35 U.S.C. 154(b) by 0 days.

(21) Appl. No.: 18/222,451

(22) Filed: Jul. 16, 2023

(65) Prior Publication Data

US 2023/0404553 A1 Dec. 21, 2023

Related U.S. Application Data

(60) Continuation of application No. 16/824,493, filed on Mar. 19, 2020, now Pat. No. 11,737,738, which is a continuation of application No. 15/586,467, filed on May 4, 2017, now Pat. No. 10,631,835, which is a division of application No. 14/269,959, filed on May 5, 2014, now Pat. No. 9,655,600.

(60) Provisional application No. 61/819,471, filed on May 3, 2013.

(51) Int. Cl.
*A61B 10/02* (2006.01)

(52) U.S. Cl.
CPC ...... *A61B 10/0291* (2013.01); *A61B 10/0266* (2013.01)

(58) Field of Classification Search
CPC .................. A61B 10/0291; A61B 10/0266
See application file for complete search history.

(56) References Cited

U.S. PATENT DOCUMENTS

| | | | |
|---|---|---|---|
| 10,201,332 B1 * | 2/2019 | Lonky | A61B 10/02 |
| 10,631,835 B2 | 4/2020 | Lee-Sepsick | |
| 2008/0208230 A1 * | 8/2008 | Chin | A61B 17/1671 |
| | | | 148/559 |

(Continued)

FOREIGN PATENT DOCUMENTS

| | | |
|---|---|---|
| CA | 2911243 | 5/2014 |
| CN | 201480038323.8 | 5/2014 |

(Continued)

OTHER PUBLICATIONS

U.S. Appl. No. 61/819,471, US, filed May 3, 2013, K. Lee-Sepsick.

(Continued)

*Primary Examiner* — Daniel L Cerioni
(74) *Attorney, Agent, or Firm* — Mary Anthony Merchant

(57) ABSTRACT

The present invention comprises methods and devices comprising a scraping element used to contact circumferentially and longitudinally the surface walls of the uterine cavity to provide for broad contact of the intended surface with the device, resulting in attainment of a sufficient volume and comprehensive tissue sample for analysis as an endometrial biopsy or screening uterine cancer. The device may provide for a reservoir for the obtained sample to be contained when removing from the uterine cavity, cervical canal, and vagina. The device may be comprised of a detachable means or be of a material that allows the user to cut the sampling head of the device for placement in collection means to maximize the amount of tissue or cells being sent to the laboratory for analysis.

14 Claims, 10 Drawing Sheets

(56) References Cited

U.S. PATENT DOCUMENTS

2013/0158429 A1* 6/2013 Lee-Sepsick ........ A61B 5/4331
600/570

FOREIGN PATENT DOCUMENTS

| EP | 147922077.1 | 5/2014 |
|---|---|---|
| IN | 11012/DELNP/2015 | 5/2014 |
| JP | 2016-512993 | 5/2014 |
| JP | 6535790 | 6/2018 |
| WO | PCT/US2014/036828 | 5/2014 |

OTHER PUBLICATIONS

U.S. Appl. No. 14/269,959/U.S. Pat. No. 9,655,600, US, filed May 5, 2014, K. Lee-Sepsick.
U.S. Appl. No. 15/586,467/U.S. Pat. No. 10,631,835, US, filed May 4, 2017, K. Lee-Sepsick.
U.S. Appl. No. 16/824,493/U.S. Pat. No. 11,377,738, US, filed Mar. 19, 2020, K. Lee-Sepsick.
Preliminary Amendment, issued May 18, 2017, in U.S. Appl. No. 15/586,467, filed May 4, 2017, Applicant: Femasys Inc., 6 p.
Restriction Requirement, issued Jan. 3, 2019, in U.S. Appl. No. 15/586,467, filed May 4, 2017, Applicant: Femasys Inc., 5 p.
Response to Restriction Requirement, issued Feb. 26, 2019, in U.S. Appl. No. 15/586,467, filed May 4, 2017, Applicant: Femasys Inc., 9 p.
NonFinal Office Action, issued Apr. 26, 2019, in U.S. Appl. No. 15/586,467, filed May 4, 2017, Applicant: Femasys Inc., 10 p.
Response to NonFinal Office Action, issued Jul. 26, 2019, in U.S. Appl. No. 15/586,467, filed May 4, 2017, Applicant: Femasys Inc., 7 p.
Final Office Action, issued Aug. 21, 2019, in U.S. Appl. No. 15/586,467, filed May 4, 2017, Applicant: Femasys Inc., 10 p.
Response to Final Office Action, issued Dec. 15, 2019, in U.S. Appl. No. 15/586,467, filed May 4, 2017, Applicant: Femasys Inc., 10 p.
Notice of Allowance, issued Dec. 20, 2019, in U.S. Appl. No. 15/586,467, filed May 4, 2017, Applicant: Femasys Inc., 5 p.
Issue Notification, issued Apr. 8, 2020, in U.S. Appl. No. 15/586,467, filed May 4, 2017, Applicant: Femasys Inc., 1 p.
Office Action, issued Jan. 31, 2019, in Canadian Patent Application No. 2911243, filing date May 5, 2014, Applicant: Femasys Inc., 3 p.
Fee Paid, issued Apr. 16, 2020, in Canadian Patent Application No. 2911243, filing date May 5, 2014, Applicant: Femasys Inc., 3 p.
Office Action, issued Apr. 19, 2017, in Chinese Patent Application No. 201480038323.8, filing date May 5, 2014, Applicant: Femasys Inc., 4 p.
Office Action, issued Nov. 18, 2018, in Chinese Patent Application No. 201480038323.8, filing date May 5, 2014, Applicant: Femasys Inc., 3 p.
Decision on Reexamination, issued Jan. 23, 2020, in Chinese Patent Application No. 201480038323.8, filing date May 5, 2014, Applicant: Femasys Inc., 1 p.
Office Action, issued Aug. 16, 2020, in Chinese Patent Application No. 201480038323.8, filing date May 5, 2014, Applicant: Femasys Inc., 1 p.
EPO Search and Opinion, issued Dec. 21, 2016, in European Patent Office Application EP2991559, filing date May 5, 2014, Applicant: Femasys Inc., 7 p.
Office Action, issued Mar. 31, 2020, in European Patent Office Application EP2991559, filing date May 5, 2014, Applicant: Femasys Inc., 4 p.
Office Action, issued Sep. 15, 2017, in Japanese Patent Application 2016-512993, filing date May 5, 2014, Applicant: Femasys Inc., 4 p.
Decision to Grant, issued May 16, 2018, in Japanese Patent Application 2016-512993, filing date May 5, 2014, Applicant: Femasys Inc., 3 p.
Decision to Grant, issued Apr. 26, 2019, in in Japanese Patent Application 2018-117008, filing date Jun. 20, 2018, Applicant: Femasys Inc., 3 p.
CN granted patent, issued Nov. 10, 2020, in CN Patent No. ZL 2014, 800383238, Applicant: Femasys Inc., 17CN1, 2 p.
Summons to Oral Proceedings, issued Mar. 17, 2022, in EP Patent Application 14792077.1, Applicant: Femasys Inc., 17EP1, 5 p.
Intention to Grant, issued Dec. 7, 2022, in EP Patent Application 14792077.1, Applicant: Femasys Inc., 17EP1, 7 p.
First Examination Report, issued Oct. 5, 2020, in Indian Patent Application 11012/DELNP/2015, Applicant: Femasys Inc., 17IN1, 6 p.
Hearing Submission, issued Nov. 16, 2023, in Indian Patent Application 11012/DELNP/2015, Applicant: Femasys Inc., 17IN1, 11 p.
Intimation to Grant, Issued Nov. 23, 2023, in Indian Patent Application 11012/DELNP/2015, Applicant: Femasys Inc. 17IN1, 1 p.

* cited by examiner

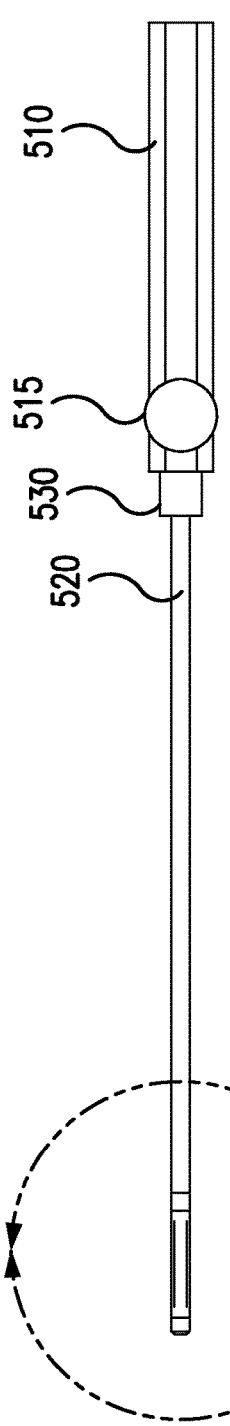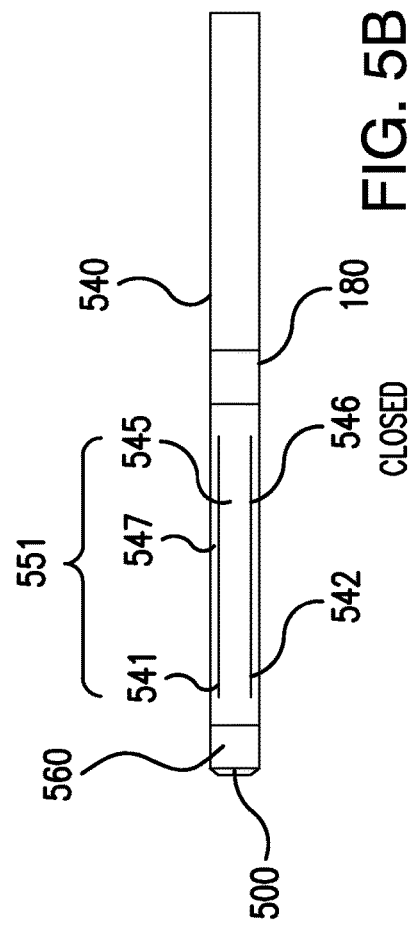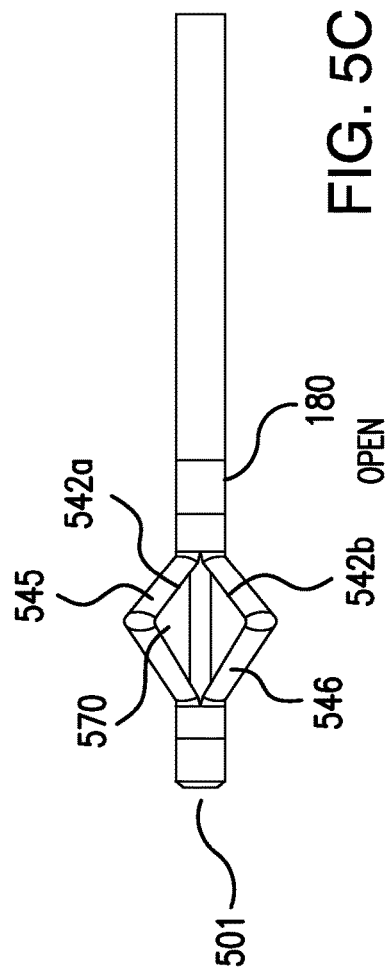

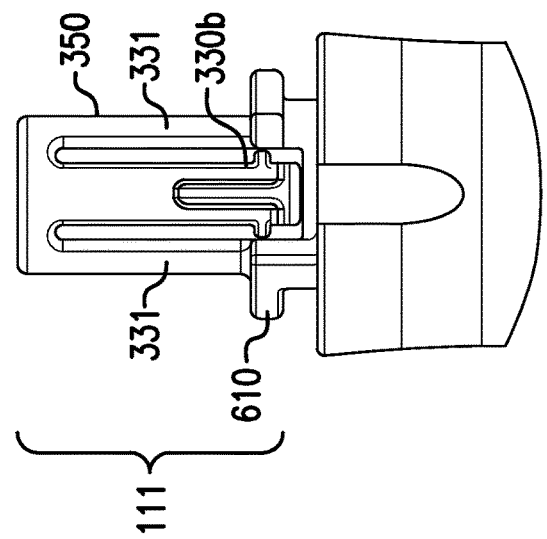
FIG. 6D
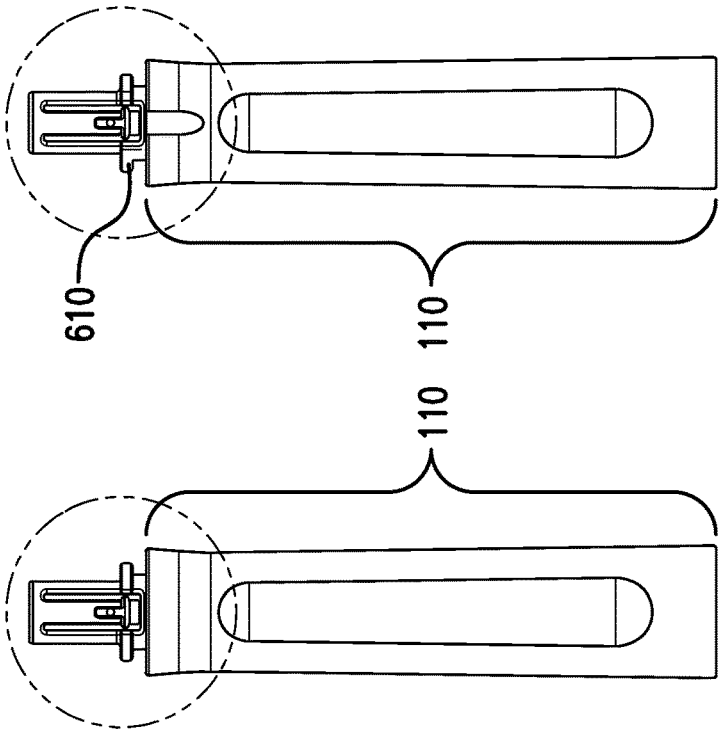
FIG. 6B
FIG. 6A
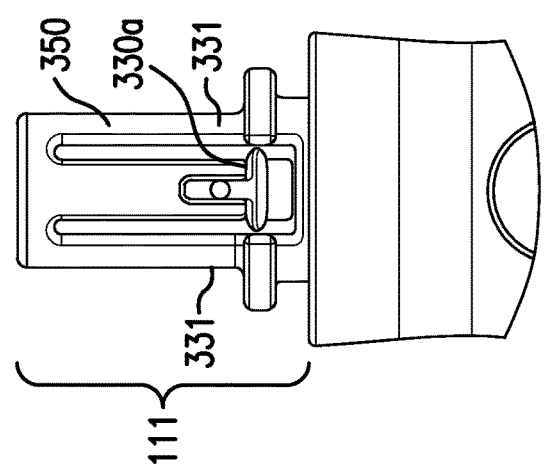
FIG. 6C

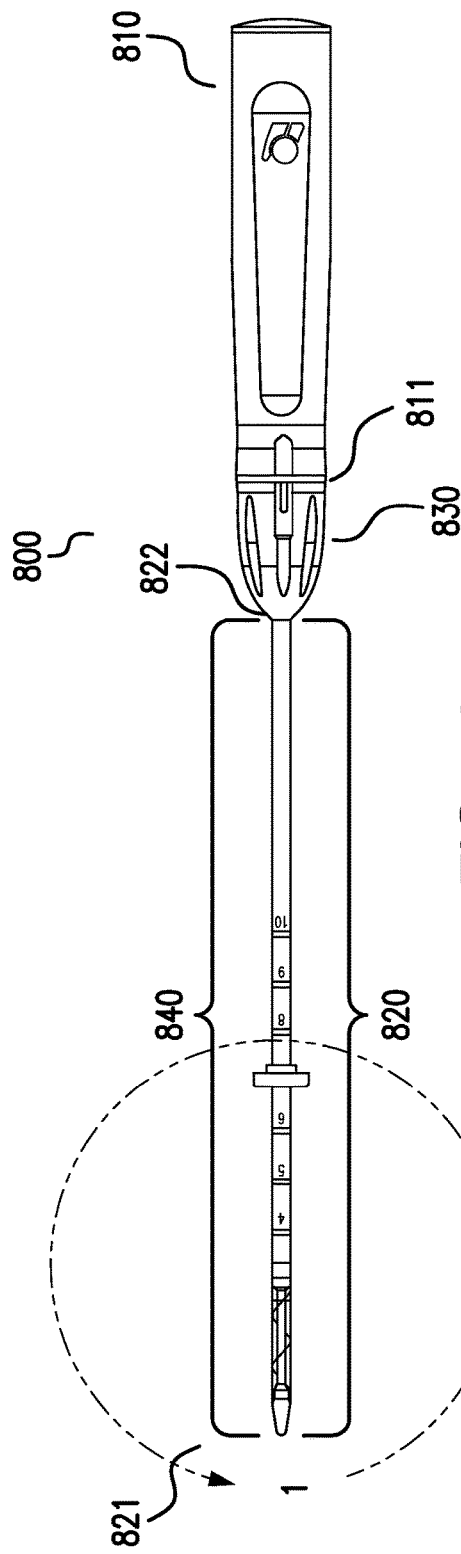
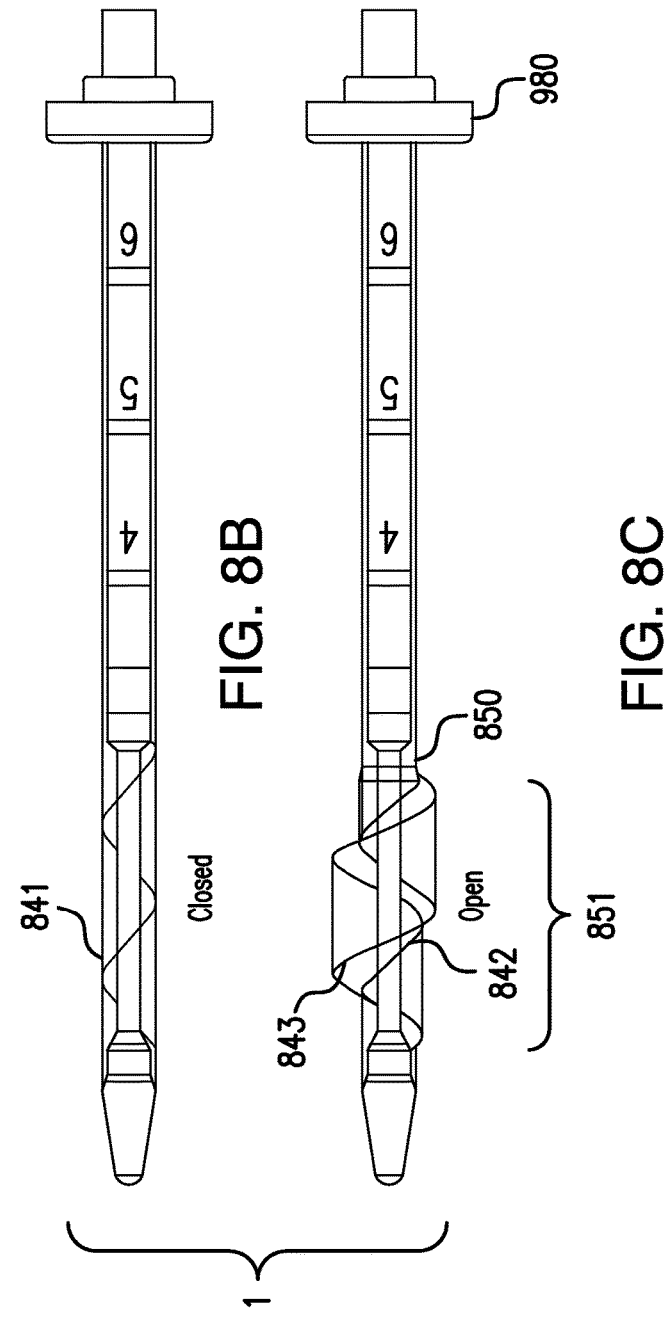
FIG. 8A
FIG. 8B
FIG. 8C

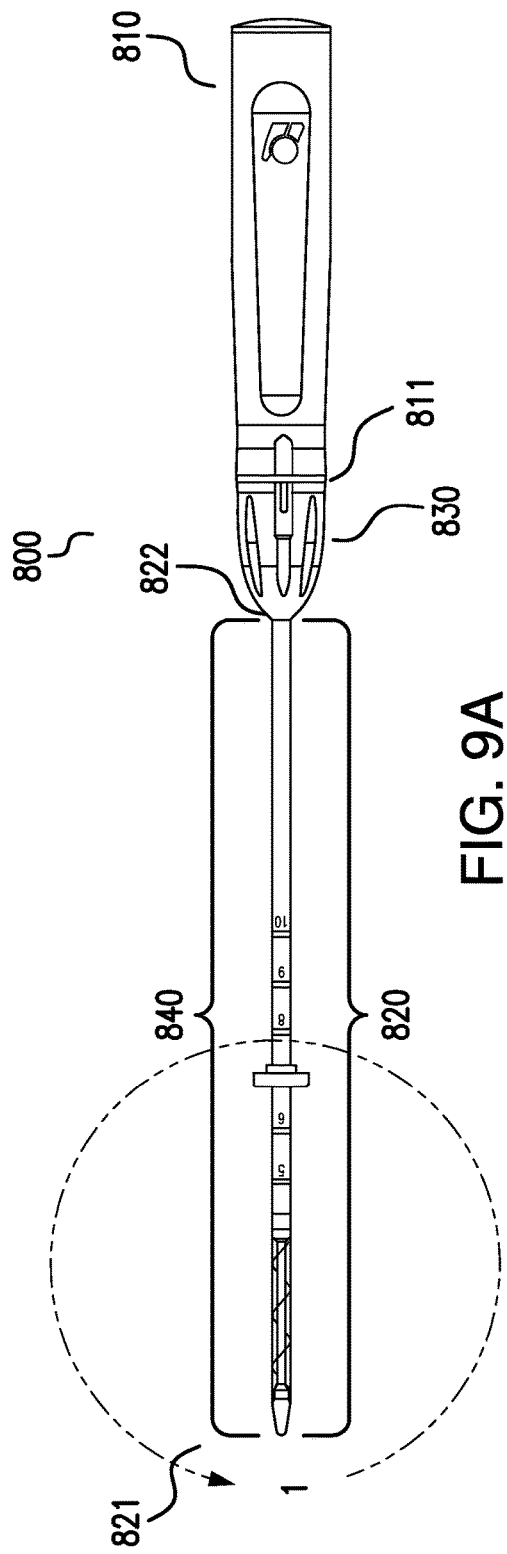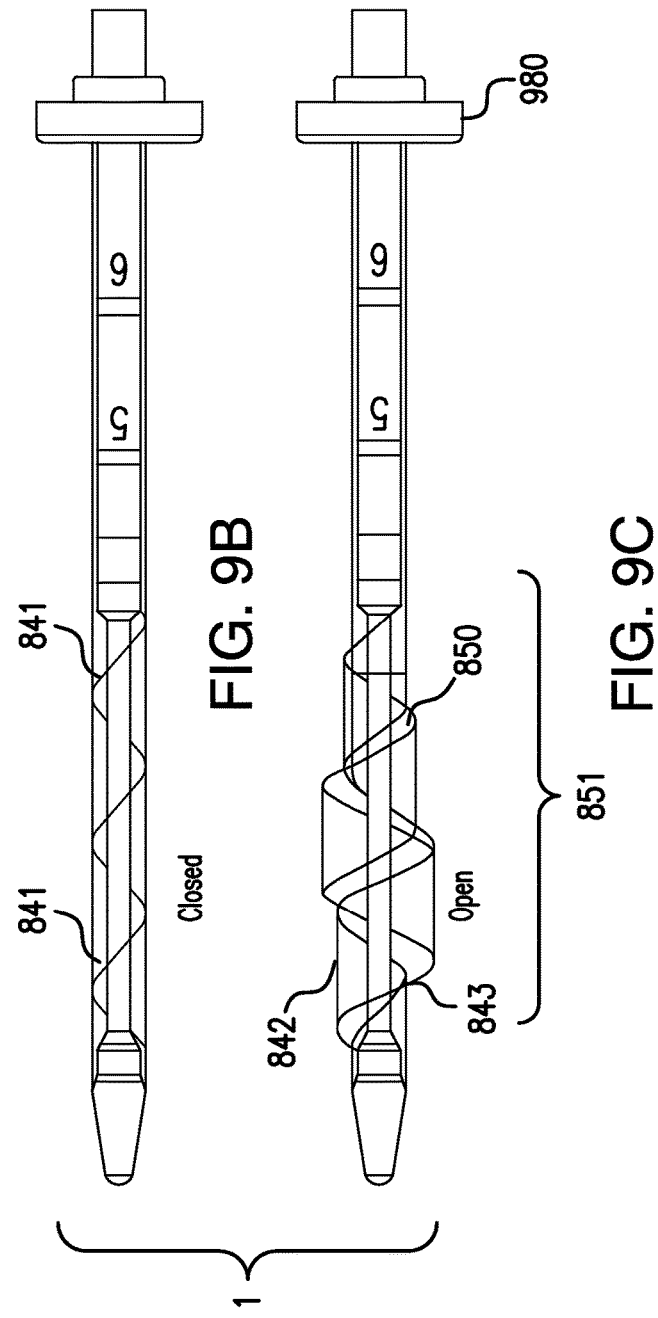
FIG. 9A
FIG. 9B
FIG. 9C

METHODS AND COMPOSITIONS FOR ENDOMETRIAL CELL AND TISSUE SAMPLING

RELATED APPLICATIONS

The present application is a continuation of U.S. patent application Ser. No. 16/824,493, filed Mar. 19, 2020, now U.S. Pat. No. 11,737,738, which is a continuation of U.S. patent application Ser. No. 15/586,467, filed May 4, 2017, now U.S. Pat. No. 10,631,835, which is a continuation of U.S. patent application Ser. No. 14/269,959, filed May 5, 2014, now U.S. Pat. No. 9,655,600, which claims the priority of and the benefit of the filing date of U.S. Provisional Patent Application Ser. No. 61/819,471, filed May 3, 2013, each of which is herein incorporated in its entirety.

TECHNICAL FIELD

The present invention relates to methods and devices for obtaining samples, simultaneously or sequentially, of cells, for example, endometrial cells.

BACKGROUND

Current methods of sampling the endometrium for cells are inadequate and may be harmful to the outcome for the patient. What is needed are methods and devices that can obtain a more complete sampling of the area without degradation of the anatomical area.

SUMMARY

Disclosed herein are methods and devices for sampling tissues, such as endometrial tissues, for example, sampling the uterine cavity for analysis as an endometrial biopsy procedure. The methods and devices may comprise only a scraping of the endometrial tissue to obtain a cellular sample, or in combination with negative pressure, scraping the uterine cavity to obtain an adequate sample. The present invention comprises sampling devices and methods that are improved over currently available devices. The present invention comprises improved sampling in the quantity of tissue and cells obtained and in the ability to broadly sample the target area, such as the endometrial lining, as the target area is assessed circumferentially and longitudinally. Additionally, the present invention comprises methods comprising devices disclosed herein for minimal contamination of the sample once it is acquired and removed from the patient. Methods and devices disclosed herein also offer improved patient outcome in that an adequate sample minimizes the need for further evaluation and additional procedures to make an assessment of the patient's condition. The invention disclosed herein provides methods and devices that decrease patient discomfort, for example, during an endometrial biopsy (EMB) procedure, and devices that sample the target area to provide accurate and sensitive detection of endometrial abnormalities. Aspects of the present invention aid in providing a more patient-oriented device that when used is more comfortable with less pain for the patient. Devices may be provided in various sizes to allow for single or minimal entry into the uterine cavity to obtain an adequate and broad sample than is found when currently available devices are used. For example, a method of the present invention comprises collecting a sample of tissue and cells from the endometrium by insertion of the device only one time into the patient's uterine cavity. Currently used devices sometimes require more than one insertion of the device into the uterine cavity to obtain adequate samples. A device of the present invention comprises a sample collection area and wand that are cylindrical in shape that captures the sample by scraping along the inner surfaces of the uterine cavity which allows for deeper and more extensive contact with the lining which is more effective in obtaining an adequate sample than utilizing a suction mechanism to pull in a sample into a device. A device of the present invention may be offered with sample collection areas of different lengths to match the anatomy of the patient. Additionally, a device of the present invention may comprise an atraumatic tip or a tapered distal tip of the wand that allows for ease of entry of the device into the endocervical canal and subsequently into the uterine cavity. The tip may provide a dilation function to aid in insertion of the device through the endocervical canal.

A device of the present invention comprises handle, a wand surrounded by a sheath, tissue sampling elements, and a sample collection cavity. The device is used for tissue and cell sampling. The device handle remains outside of the patient while the sample collection cavity and tissue sampling elements are placed in proximity to the target area. A target area may be an endometrial surface. The wand is an elongated body (tubular or solid) that is designed to traverse along the entire length or partial length of the inner circumference of the sheath. In embodiments presented herein, the wand is connected to a handle for manipulation of the entire device and the handle may incorporate components to expand the sampling area, comprising tissue sampling elements and a sample collection cavity to allow for scraping of the target area, such as the endometrial lining, both circumferentially and longitudinally, against the inner surface of the uterine cavity to obtain tissue or cells. The sheath of a device of the present invention may be an elongated tubular body designed to allow for an inner shaft to traverse the sheath's inner circumference. The sheath may function to protect the tissue sample from contamination, and may provide the tissue sampling elements by which the sampling is achieved (i.e. serves to scrape the uterine cavity), protect the sample from being lost during retraction of the device through the cervical os, and/or aid in device placement. The sampling area comprises the portion of the device where the tissue sampling elements. such as opposing edges of a slit are used as scraping edge(s), are located. The sampling area provides for capturing the tissue and endometrial cells located in the uterine cavity.

DESCRIPTION OF FIGURES

The accompanying figures, which are incorporated in and constitute a part of this specification, illustrate several aspects and together with the description serve to explain the principles of the invention.

FIG. 5A-C shows an exemplary device of the present invention, where 5B and 5C are an enlargement of the distal portion of the exemplary device shown in 5A.

FIG. 6A-D shows the distal end of the handle of a device of FIGS. 1 and 3, wherein A is a front view, C is an enlargement of A, B is a back view and D is an enlargement of B.

FIG. 8A-C is an exemplary example of a device of the present invention.

FIG. 9A-C is an exemplary example of a device of the present invention.

Figure 1:
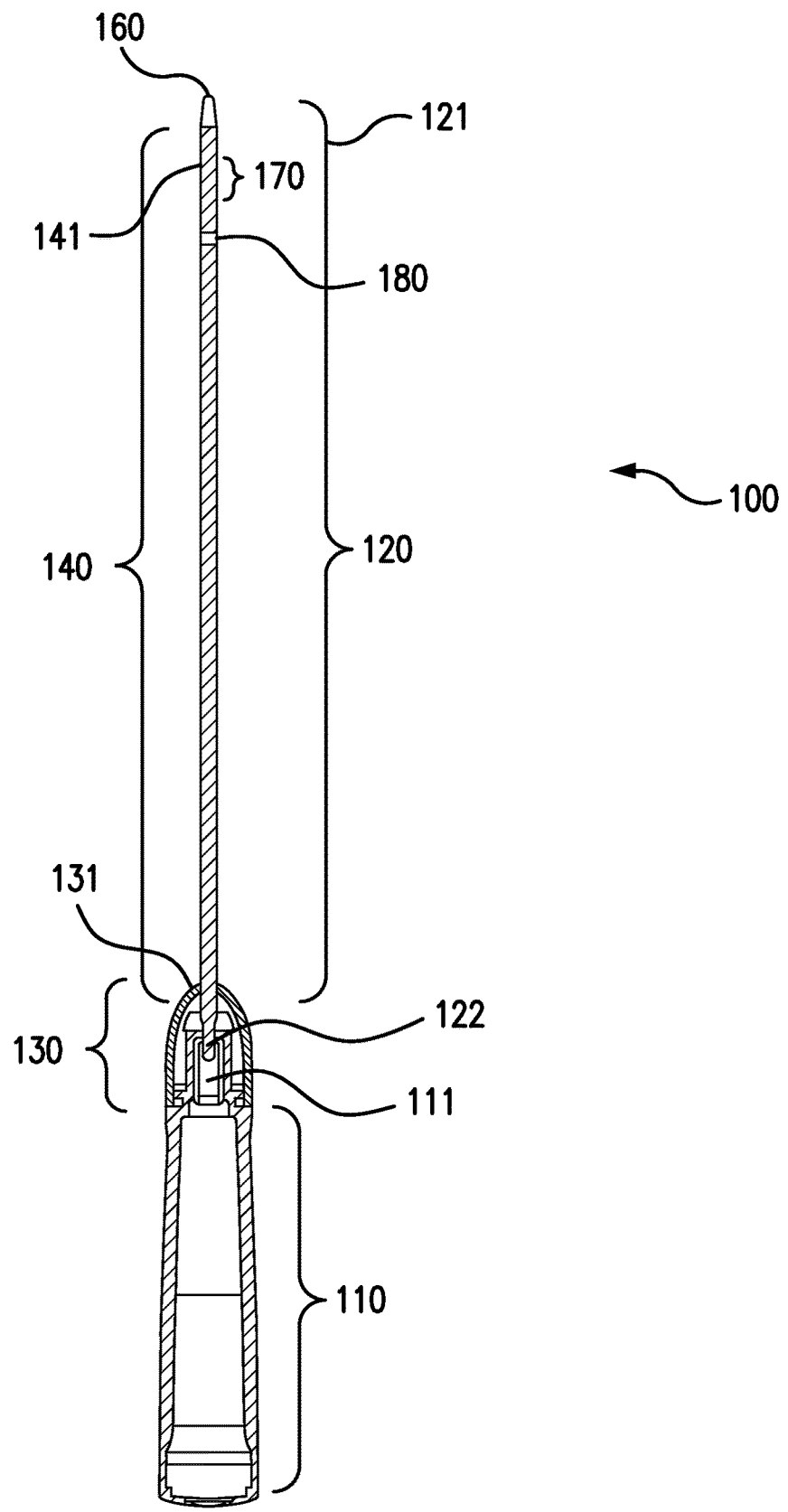
FIG. 1 shows an exemplary example of a device of the present invention.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are methods and devices for cell sampling. The present invention provides for collection of cell and tissue samples from an area of interest within an organ or tissues, such as the uterine cavity, by having an expandable aspect which allows for broad contact, such as circumferentially to the inner surface of the walls of the uterine cavity, with capture of a sufficient sample volume for analysis and minimal contamination of the sample collected. The diagnosis of pre-malignancy and malignancy is dependent on the quantity and broad representation (a sufficient number of cells to be of diagnostic value) of the targeted area with the purest sample obtained. Obtaining an adequate sample is usually difficult as the customary available devices utilize suction to withdraw a sample from a limited area that often is rendered not adequate for diagnosis. The present invention allows the user to obtain a broad, representative and more substantive sample with minimal contamination from a patient with one or a few entries and removals from the patient.

An aspect of the present invention comprises an expandable sampling area comprising tissue sampling elements and a sample collection cavity. A tissue sampling element may comprise opposing edges of a slit. Providing a device having an expanding sampling area provides for the insertion of the device and the collection of the sample to occur substantially along one plane or a single line of entry into the patient. Once inserted, a device of the present invention may be rotated around the single line of entry to collect a sample circumferentially and/or may be moved longitudinally in a distal to proximal direction or proximal to distal direction to collect a sample. A method of using a device of the present invention comprises insertion of the device and collection of the sample along a single plane or a single line of entry into the patient, wherein the rotation occurs in a fixed location with a very small to no rotational diameter of the wand and handle. In collecting a sample using currently available devices, not one of the present invention, a device end having a sampling area is inserted into a patient and then the sampling area is moved within the uterine cavity by the device, such as the insertion member and handle, being rotated through a large arc or circle to apply pressure to the sampling area. The rotation of the insertion member and the handle is not around a single line of entry, but comprises a large rotational area that comprises a large rotational diameter, and resembles a geometric cone with the sampling area at the apex of the cone and the large rotational diameter due to movement of the handle at the base of the cone.

In an aspect, the small to no rotational diameter of a device of the present invention is due to the expandable nature of the tissue sampling elements of a device of the present invention. Before insertion of a device of the present invention into a patient, a tissue sampling element comprising opposing edges of a slit are aligned with the outer surface of the sheath, which is referred to herein as the closed position. In the closed position, the entire sheath has a substantially uniform diameter from the proximal end to the distal end of the sheath. Once the sampling area of the device is in place in the cervical canal or uterine cavity, the slit (or slits) is opened, exposing the opposed edges of a slit and creating the tissue sampling element of the device. There is no need to rotate the entire device in geometric cone shaped rotation because the expanded tissue sampling element contacts the inner surface of the uterine cavity, a potential space. The opposed edges of the slit or slits are then rotated with a small to no rotational diameter along the single line of entry and because the expanded opposed edges of the slit or slits are in contact with the inner surface of the uterine cavity, the sample is scraped or cut from the inner surface by the edges and collected within the sample collection cavity. Once the sample is within the sample collection cavity, the slit or slits are moved to the closed position, so that the opposing edges are substantially adjacent to each other and the sample collection cavity is substantially covered so that no sample within the sample collection cavity can exit and no cellular material from outside the sample collection cavity can enter the cavity, which prevents contamination of the sample.

Having an expandable tissue sampling element also provides more contacting surface within the uterine cavity than is possible with currently available devices. For a currently available device, which does not have an expandable scraping element, the thin tube, which is designed to be small enough to go through the cervical canal, utilizes an opening at the end of the tube and provides suction at that opening to withdraw tissue for a sample of a limited area. When in place in the uterine cavity, a vacuum is established within the device by manually retracting its internal piston and the device is rotated between the fingers and it is passed several times between the fundus and the internal cervical os. This type of suction forces limited tissue and cells from the uterine cavity, which is at least uncomfortable and generally painful for a patient, and the sample obtained is often determined to be not adequate for diagnosis.

A method of the present invention comprises obtaining a sample of the endometrium of the uterine cavity by using a device comprising a sampling area comprising an expandable tissue sampling element. A device of the present invention comprises an expandable tissue sampling element. A device of the present invention comprises a sampling area comprising an expandable tissue sampling element comprising a sheath having at least one slit comprising two opposing edges wherein the two opposing edges may be moved apart from each other to expand the diameter of sheath so that the diameter of the sheath is greater where the two opposing edges are moved apart from each other than the diameter of the sheath where there is no slit. An expandable tissue sampling element is expanded by the movement of the opposing edges of a slit away from each other and the tissue sampling element is reduced to its original state by the opposing edges of a slit moving together and being adjacent again. When the slit is open, so that the opposing edges of the slit are apart from one another, the sheath and/or sampling area is said to be expanded. When the slit is closed, so that the opposing edges of the slit are substantially adjacent to one another, the sheath and/or sampling area is not expanded.

The standard management of patients with abnormal uterine bleeding, postmenopausal bleeding, suspected uterine cancer, AGUS (abnormal glandular cells of unknown significance) as determined by pap smear, chronic anovulation, those undergoing an endometrial ablation or are infertile where the lining can determine ovulation (i.e. endometrial dating) is an endometrial biopsy (EMB). An endometrial biopsy is the most commonly performed test to assess the presence of endometrial hyperplasia or endometrial cancer.

It is common for endometrial tissue sampling to result in findings that are insufficient for diagnosis. In studies of patients with postmenopausal bleeding, the range of sampling failure (i.e. inadequate sample or inability to perform the biopsy) with Pipelle biopsy was 0-54% as noted by the Committee on Gynecologic Practice (ACOG Committee Opinion, August 2009). When endometrial biopsy is performed and tissue is reported as insufficient for diagnosis, some further examination is necessary, which may include transvaginal ultrasonography. If the endometrial biopsy sample doesn't provide enough tissue, or if the biopsy suggests cancer but the results are uncertain, a D&C (dilation and curettage) is performed. In this outpatient procedure, the opening of the cervix is enlarged (dilated) and a special instrument is used to scrape tissue from inside the uterus. This may be done with or without hysteroscopy. The procedure takes about an hour and may require general anesthesia or conscious sedation either with local anesthesia injected into the cervix or with spinal or epidural blocking anesthesia. A D&C is usually done in an outpatient surgery area of a clinic or hospital. Most women have little discomfort after this procedure. A D&C procedure is costly and invasive and would not be necessary if the endometrial biopsy captured an adequate sample for analysis.

A number of devices have been developed to collect samples from the uterine cavity, including Novak's curette, Vabra aspirator, Masterson endometrial biopsy system and Pipelle device (most commonly used). These devices incorporate a means of suction to obtain the tissue sample, whether by syringe, a device that generates a vacuum, a reusable hand operated pump, or an internal piston that is manually retracted to create a vacuum for sample collection.

Although, cytologic screening reduces mortality from uterine cancer by earlier diagnosis of invasive disease, there is still an unacceptable sample inadequacy rate due to the suction devices used and the method by which a sample is obtained. The current EMB devices obtain a questionable sample that is inadequate for pathological evaluation, at the expense of subjecting the patient to one or more subsequent, more invasive procedures. This inadequate finding often leads to unnecessary dilation & curettage or other transvaginal procedures. Furthermore due to the current device designs it is unlikely that a broad sample of the uterine cavity will be obtained so detection of pre-cancerous or cancerous cells may be missed.

The currently used or available device designs have inherent deficiencies that affect their ability to be a reliable and useful tool in diagnosing endometrial hyperplasia or endometrial cancer. The ideal EMB device is one that is simple, broad contacting, and most importantly provides an adequate volume sample of the endometrial lining of the uterine cavity that is minimally contaminated. The devices of the present invention comprise easy to use devices that are applicable to a variety of anatomical uterine cavity variants, which decrease the frequency of inadequate sample findings, which allow for improved detection rates of early high grade lesions, and that decrease the number of unnecessary additional treatments.

The present invention comprises methods and devices useful for obtaining the intended tissue sample of a body conduit under controlled conditions, for example, where the tissue are located in the uterine cavity. For example, the present invention comprises methods and devices for use in capturing a broad, adequate, and minimally contaminated sample with single or minimal number of entry insertions into the uterine cavity. The devices can be designed to be reusable or disposable for single use. As used herein, broad means that the sample comprises cells and tissues from a representative area of the organ that provide a more accurate diagnosis of the condition of the organ, as compared to currently available devices having one opening or a port oriented in one direction, which then contacts a small, limited area of the endometrium. For example, a broad sample would comprise a representative sample of the cells or tissue in that general area of the organ. The sample may be broad and encompass a representative sample by sampling from the area of the organ contacted by insertion of the sampling area into the uterus and expanding the tissue sampling element in that area contacted, or the tissue sampling element may be moved in one or more directions, in contact with the endometrium, to obtain a sample of cells or tissue in the entire area contacted.

A device of the present invention may be a sterile, disposable endometrial sampling device with indications for single patient use in obtaining tissue samples from the uterine cavity for histological analysis. Clinical indications for performing a method of the present invention using a device disclosed herein include, but are not limited to, further evaluation of abnormal glandular cells of unknown significance (AGUS) as determined by pap smear; further evaluation of abnormal uterine bleeding, including post-menopausal bleeding; as a diagnostic device in patients suspected of uterine cancer; for chronic anovulation; prior to those undergoing an endometrial ablation procedure; for patients who are infertile where the lining can determine ovulation (i.e. endometrial dating); or with other clinical sequelae. A device of the present invention may collect a targeted broad tissue sample with minimal contamination that is adequate in volume for histological evaluation. A device of the present invention may comprise a wand that is somewhat rigid and one directional (not bent) or a wand may be bendable, or bent, so that an area of interest is contacted by the expandable sampling area.

A device of the present invention comprises a sampling area comprising a sample collection cavity comprising a portion of a wand having a reduced diameter and an overlaying sheath member having at least one slit that is capable of providing an opening within the sheath member for access to the sample collection cavity beneath. The slit may have two opposing edges. There may be one or more slits in the sheath member forming one or more access sites to the sample collection cavity. The slit may be in an open or closed position. In a closed position, the opposing edges of the slit are adjacent and adjoin each other so as to substantially close the slit and to prevent access to the sample collection cavity underlying the slit or slits. In an open position, the opposing edges of the slit are apart from each other to form an opening so that the sample collection cavity may be accessed. In an aspect, when the opposing edges moved apart from each other, the diameter of the area of the sheath where the slit occurs is greater than the diameter of the area of the sheath where the slit occurs when the opposing edges are substantially adjoined or a closed position. The open position is also referred to herein as being expanded. When the opposing edges of a slit are moved apart from each other, each edge is exposed and forms a scraping edge, and the opposing edges form a tissue sampling element that is used to remove tissue from a soft tissue location. The removed tissue enters the sample collection cavity through the opening formed by the moved apart opposing edges. The removed tissue (a sample) is contained within the sample collection cavity and the opposing edges are moved together to substantially close the sample collection cavity so that no further tissue can enter the sample collection cavity to contaminate the sample and so that the sample does not leave the sample collection cavity and be lost.

Description of Device

The present invention comprises a device for sampling a tissue, for example the uterine cavity comprising endometrial lining. A device of the present invention is not limited to sampling a tissue and collecting cells as described herein for uterine sampling, but may be used for sampling tissues and obtaining cells from any tissue as may be used by those of skill in the art. The present invention is not limited to only the examples disclosed herein but may be used in methods of cellular sampling contemplated by those of skill in the art.

Figure 2A:
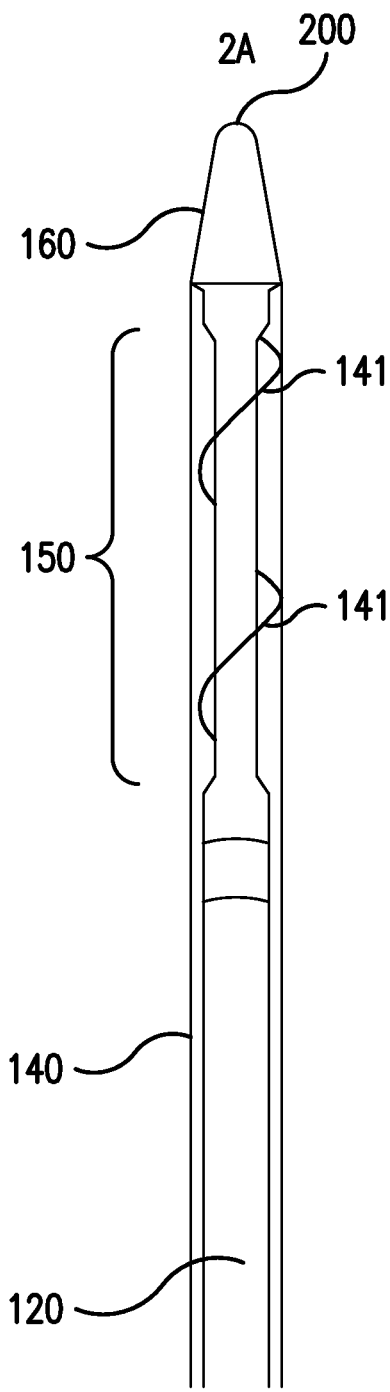
FIGS. 2A and B shows an enlarged view of a sampling area of the device of FIG. 1.
Figure 2B:
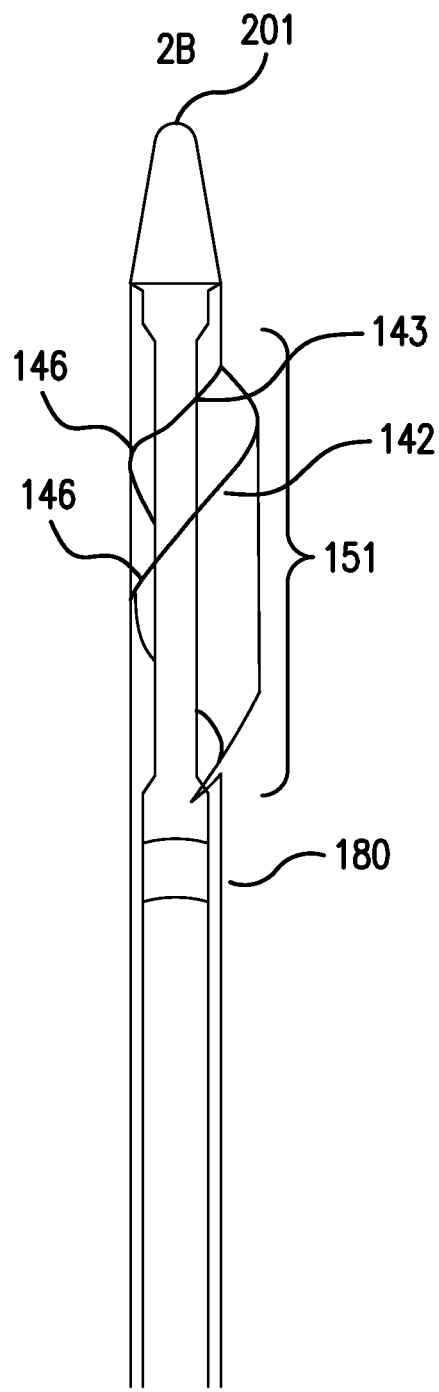
Figure 3A:
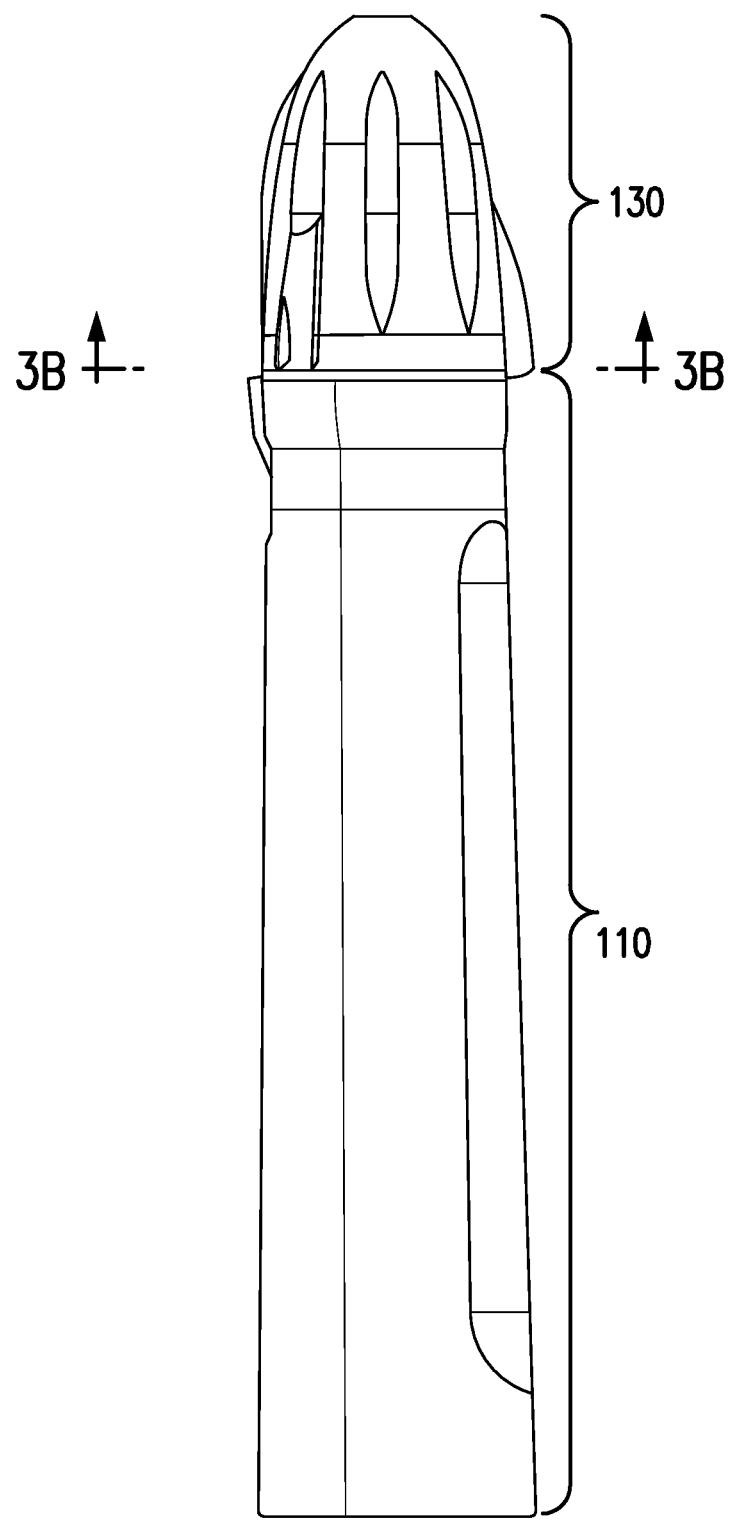
FIGS. 3A and B shows an enlargement of the handle and actuator portions of the device of FIG. 1, wherein 3A is an exterior view and 3B is a cross-sectional interior view.
Figure 3B:
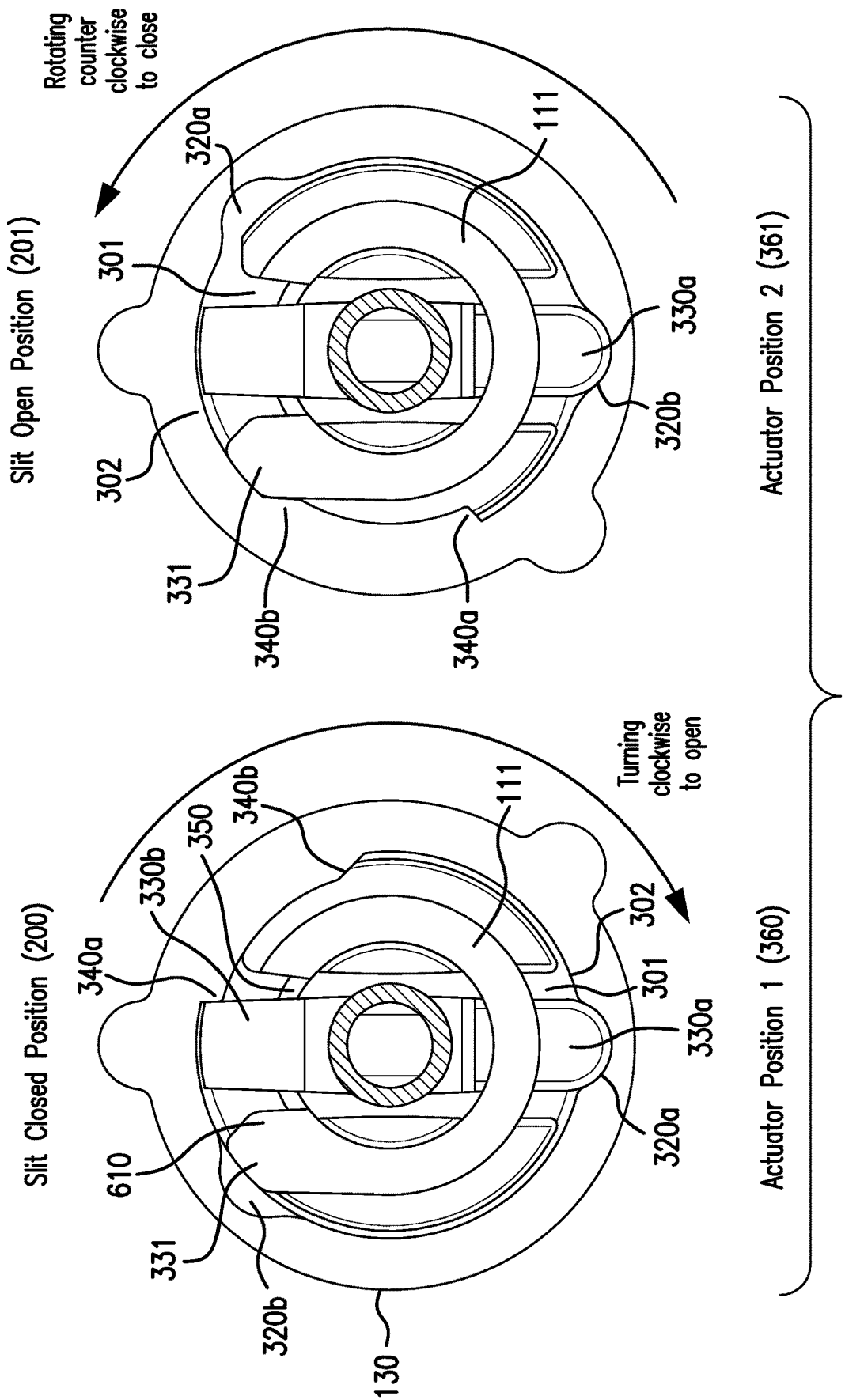
Figure 4:
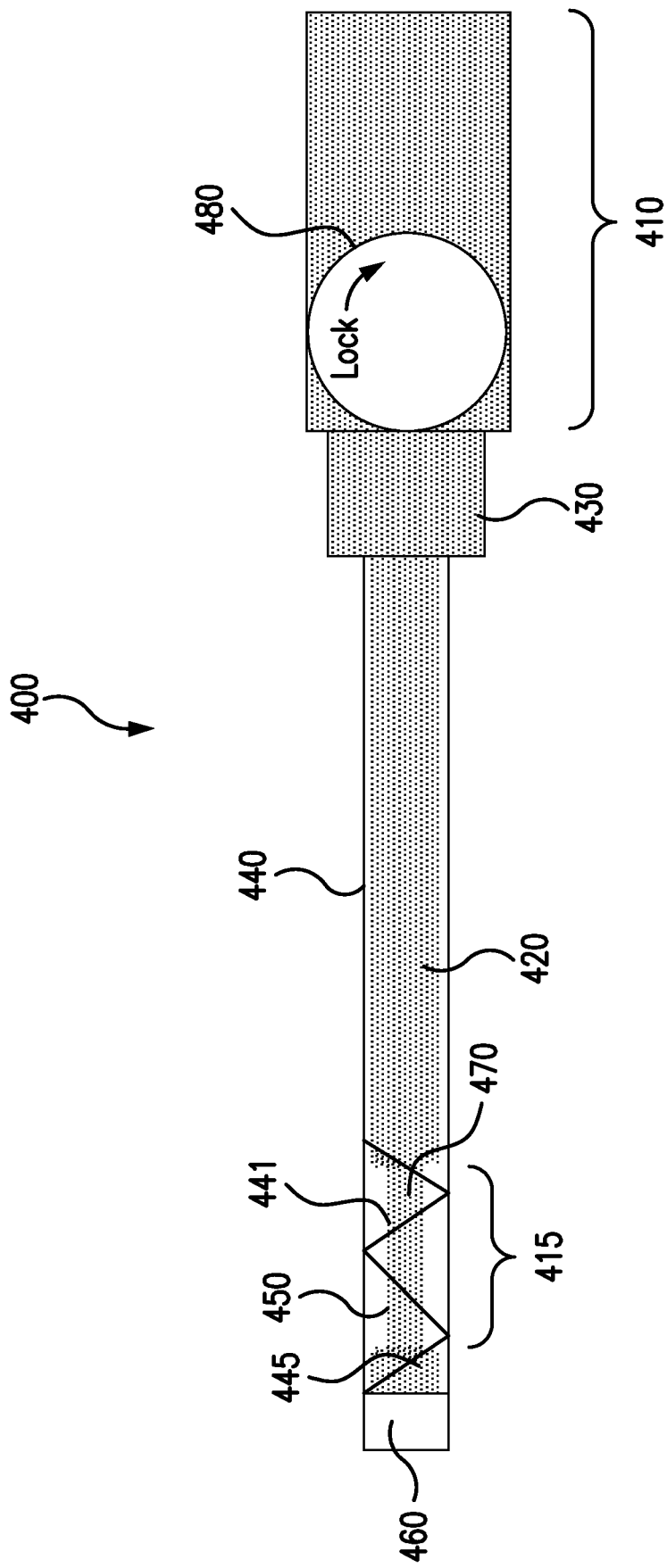
FIG. 4 shows an exemplary device of the present invention.
Figure 7:
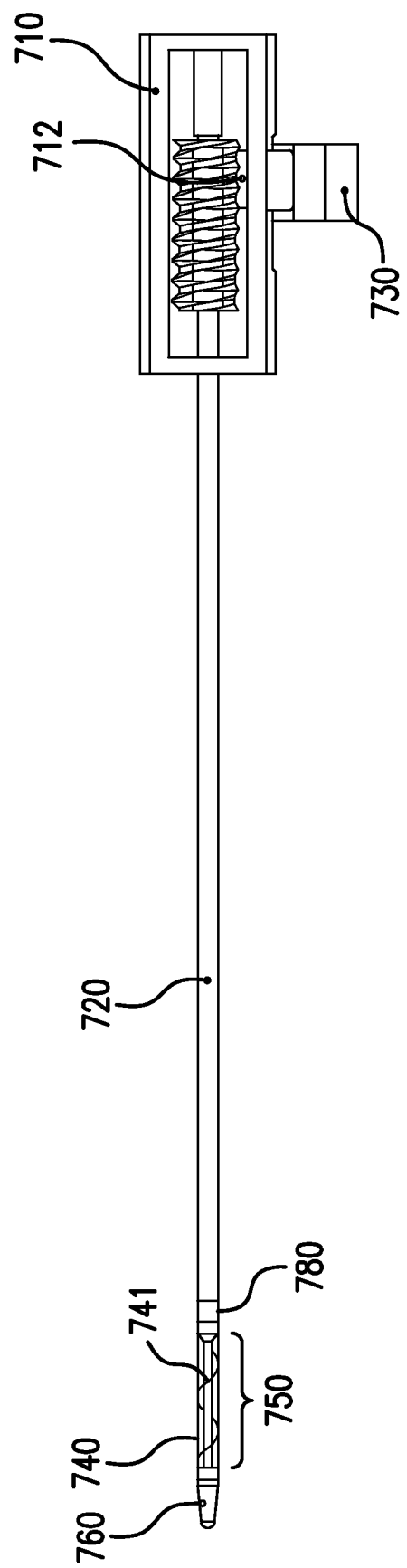
FIG. 7 is an exemplary example of a device of the present invention.

An exemplary device is shown in FIGS. 1, 2, 3 A and B, and 6, 8A-C and 9A-C, and exemplary devices are shown in FIG. 4, FIG. 5 and FIG. 7, and described herein. Looking at FIG. 1, a device of the present invention comprises a endometrial sampling apparatus 100, comprising, a handle 110 having a distal end 111 and a longitudinal axis, an elongated wand 120 extending outwardly from the distal end 111 of the handle 110 substantially along the longitudinal axis, wherein the wand 120 has an exterior surface, a front end 121 and a back end 122, and wherein the back end 122 is fixedly mounted to the distal end 111 of the handle 110; an actuator member 130 rotatively coupled to the distal end 111 of the handle 110, the actuator member 130 defining an opening at a first end 131 that is sized to rotatively receive a portion of the wand; a sheath member 140 selectively encapsulating a portion of the wand 120 and fixedly mounted to a portion of the wand proximate to the front end 121 of the wand and to a portion of the first end 131 of the actuator member 130, wherein the sheath member 140 defines a slit 141 on a distal end portion of the sheath member 140, the slit 141 being bordered by opposing edges 142 and 143, (see FIG. 2) wherein the distal end portion of the sheath member 140 and a portion of the exterior surface of the wand underlying the distal end portion of the sheath member define a sample collection cavity 150. As shown in FIG. 2, the slit 141 is selectively movable (expandable) between a closed position 200, (FIG. 2A) in which the opposing edges 142 and 143 of the slit 141 substantially adjoin to substantially seal the sample collection cavity 150, and an open position 201, (expanded) (FIG. 2B) in which the opposing edges 142 and 143 of the slit 141 are spaced from each other for obtaining a tissue sample when positioned within a uterine cavity by contacting the surface of the endometrial lining. When spaced apart from each other, the opposing edges 142 and 143 form a tissue sampling element such that when contacting a soft tissue surface is capable of removing tissue from a soft tissue surface, such as the inner surface of the uterine cavity. As shown in 2B, the sampling area 151 comprises an open sample collection cavity 150 with opposing edges 142 and 143 forming the tissue sampling element 146. Optionally, spaced from the proximal end of the sample collection cavity 150 is an indicator 180, which may be used as a depth indicator to a user to indicate the length of the apparatus inserted into the patient and approximate location of the sample collection cavity 150. A depth stop, not shown, may be placed on or proximate to the indicator 180. The device may comprise a closed tip 160, which may be an atraumatic tip.

As shown in FIGS. 3A and B, actuator member 130 is selectively rotatable about the distal end 111 of the handle 110 between a first position 360, in which the slit 141 is positioned in the closed position 200 (shown in FIG. 2A), and a second position 361, in which the slit 141 is positioned in the open position 201 (FIG. 2B). The slit 141 may be a helical slit 141 that extends about the longitudinal axis. The helical slit may comprise a plurality of helical slits. A slit may have at least one round 170 around the longitudinal axis. (See FIG. 2) The opposing edges 142 and 143 of the slit 141 may be oriented substantially parallel to each other and substantially normal to an exterior surface of the sheath member 140 when the slit 141 is in the closed position 200. At least a portion of one of the opposing edges 142 and 143 of the slit 141 is oriented at an acute angle to the longitudinal axis when the slit 141 is in the open position 201. The opposing edges 142 and 143 of the slit may be oriented substantially parallel to each other and are positioned at a face angle relative to an exterior surface of the sheath member 140 when the slit 141 is in the closed position 200. At least a portion of one of the opposing edges 142 and 143 of the slit 141 may be oriented at an acute angle to the longitudinal axis when the slit 141 is in the open position 201. In an aspect, the face angle is not normal to the exterior surface of the sheath member 140.

In an aspect, the front end of the wand 120 defines an atraumatic tip 160. (See FIGS. 1 and 2). The atraumatic tip 160 may be tapered for ease of entry of a device into the cervical os. The atraumatic tip 160 may be made from the same or a different material as the wand, and may be more flexible than the wand for patient comfort. The distal end portion of the sheath member 140 is positioned proximate to the atraumatic tip 160 of the wand 120.

In an aspect, a portion of the wand 120 has a reduced diameter. In an aspect, the portion of the wand 120 having a reduced diameter underlies the distal end portion of the sheath member. In an aspect, the portion of the wand 120 having a reduced diameter underlies the distal end portion of the sheath member where a slit 141 is located. In an aspect, the portion of the wand 120 having a reduced diameter and the distal end portion of the sheath member 140 where a slit 141 is located define a sample collection cavity 150.

See FIG. 3A which shows the exterior surface of handle 110 and actuator 130. FIG. 3B shows the interior view of actuator 130 as seen by looking from the handle towards the actuator in a distal direction, as sectioned along the line shown in FIG. 3A. In an aspect, actuator 130 defines an interior cavity 301 having an interior peripheral edge 302 having a plurality of spaced indentations 320 (320a and b) defined thereon and one or more actuator protrusions 340 (e.g., 340a and 340b). An actuator protrusion 340, when interacting with the distal end 111 of handle 110, may prevent the actuator 130 from continuing to rotate in a particular direction, depending on the location of the actuator protrusion. For example, when actuator 130 is in Position 1 (360), protrusion 340a stops actuator 130 from rotating further in a counterclockwise direction. Similarly, when actuator 130 is in Position 2 (361), actuator protrusion 340b stops actuator 130 from rotating further in a clockwise direction.

Looking at FIGS. 3B and 6, the distal end of the handle 110 defines a handle protrusion 350 extending distally along the longitudinal axis, the handle protrusion 350 defining a plurality of radially biasable keys 330 and a stationary portion 331. The radially biasable key 330a is configured to be selectively received therein the plurality of indentations 320 (e.g., 320a and 320b) in the respective first 360 and second 361 positions. A shown in FIGS. 3A and 6, key 330a is rounded so as to fit within a rounded indentation 320a and 320b. Key 330b acts as a radially biasable key during assembly of the device and then it acts as a non-biasable key during device operation since it does not interact with the spaced indentations 320 during actuation/rotation. Stationary portion 331 provides a stop 610 to impede the movement of actuator 130. In an aspect, the plurality of spaced indentations 320 comprise a pair of spaced indentations 320 positioned between about 110° to 140° apart. In an aspect, the plurality of radially biasable keys 330 (e.g., 330a and 330b) comprise a pair of spaced radially biasable keys 330 positioned between about 170° to 190° apart. In an aspect, the pair of spaced radially biasable keys 330 are positioned about 180° apart. In an aspect, moving the actuator position from closed 360 to open 361 requires a rotation between about 220° to 250°.

Optionally, the elongate wand 120 is flexible. See for example, FIG. 1. Optionally the distal end of the device comprising the sampling area 151 is detachable. For example, (not shown) the distal ends of the sheath and shaft, comprising the sampling area 151, both could be scored so that with pressure or cutting, they break away from the rest of the device. A scored line around the diameter of the shaft could be used to create a weak section in the shaft so that the shaft would break when flexed. Depending on the sheath material, the sheath may or may not need to be scored also. In an aspect, the sampling area could be removed intact by cutting it off with a cutting tool or knife. Alternatively, the tip of the device could be sheared off using, a cutting tool.

As shown in FIGS. 1 and 2, a device of the present invention comprises a endometrial sampling apparatus 100 comprising, a handle 110 having a distal end 111 and a longitudinal axis; an elongate wand 120 extending outwardly from the distal end 111 of the handle 110 substantially along the longitudinal axis, wherein the wand 120 has an exterior surface, a front end 121 and a back end 122, and wherein the back end 122 is fixedly mounted to the distal end 111 of the handle 110; an actuator member 130 rotatively coupled to the distal end 111 of the handle 110, the actuator member 130 defining an opening at a first end 131 that is sized to rotatively receive a portion of the wand 120; a sheath member 140 selectively encapsulating a portion of the wand 120 and fixedly mounted to a portion of the wand proximate the front end 121 of the wand 120 and to a portion of the first end 131 of the actuator member 130, wherein the sheath member 140 defines a slit 141 on a distal end portion of the sheath member 120, the slit 141 being bordered by opposing edges 142 and 143, wherein the slit 141 is selectively movable between a closed position 200, in which the opposing edges 142 and 143 of the slit 141 substantially adjoin to substantially seal a sample collection cavity 150, and an open position 201, in which the opposing edges 142 and 143 of the slit 141 are spaced from each other for selectively obtaining a tissue sample when positioned within a uterine cavity. In an aspect, the actuator member 130 is selectively rotatable about the distal end 111 of the handle 110 between a first position 360, in which the slit 141 is positioned in the closed position 200, and a second position 361, in which the slit 141 is positioned in the open position 201. In an aspect, the distal end portion of the sheath member 140 and a portion of the exterior surface of the wand 120 underlying the distal end portion of the sheath member define a sample collection cavity 150. Optionally, an indicator 180 is located proximally to sample collection cavity 150. In an aspect, the slit 141 is a helical slit that extends about the longitudinal axis. A slit 141 may have at least one round 170 around the longitudinal axis.

As shown in FIGS. 3B and 6, in an aspect, actuator 130 defines an interior cavity 301 having an interior peripheral edge 302 having a plurality of spaced indentations 320 defined thereon, wherein the distal end 111 of the handle 110 defines a handle protrusion 350 extending distally along the longitudinal axis, the handle protrusion 350 defining a plurality of radially biasable keys 330, of which 330a is configured to be selectively received therein the plurality of spaced indentations 320 in the respective first 360 and second 361 positions. In an aspect, the plurality of spaced indentations comprise a pair of spaced indentations 320 (e.g., 320a and 320b) positioned between about 110° to 140° apart. In an aspect, the plurality of radially biasable keys comprises a pair of spaced radially biasable keys 330 (e.g., 330a and 330b) positioned between about 170° to 190° apart. In an aspect, the pair of spaced radially biasable keys 330 are positioned about 180° apart. In an aspect, moving the actuator position from closed 360 to open 361 requires a rotation between about 220° to 250°.

As shown in FIG. 3B, actuator 130 is moved from position 1 (360) to position 2 (361) by rotating actuator 130 around the handle 110 in a clockwise direction. Biasable key 330a is present in indentation 320a in position 1, and when the actuator 130 is rotated in a clockwise direction to position 2 (361), biasable key 330a then resides in indentation 320b. In position 1, actuator protrusion 340a abutting key 330b prevents actuator 130 from rotating in a counterclockwise direction. In position 2, actuator protrusion 340b abutting stop 610 formed in stationary portion 331 prevents actuator 130 from rotating in the clockwise direction. Handle protrusion 350 does not rotate, though keys formed therein may be biased radially, but the handle protrusion 350 remains in one location (other than biasable keys moving inward and returning to the starting position radially) and interacts with the actuator protrusions and indentations.

FIG. 4 shows an embodiment of the present invention comprising a sample collection cavity 450 formed by a distal section of the wand 420 having a reduced diameter 470 and the overlying sheath 440, and having a sample area 415 comprising an expandable tissue sampling element formed by a slit 441 comprising two opposing edges, which when moved apart from each other form a tissue sampling element. The device comprises a wand 420 and an overlying sheath member 440, a slit 441 in the distal portion of the sheath member, a handle 410 and a tip 460.

In a device of the present invention, a sheath may be moved, and a slit may be opened, in a variety of methods, and the present invention is not limited to only those exemplified herein. Moving a sheath member to affect the opposing edges of one or more slits, so that the opposing edges move apart from each other, may be accomplished using an actuator, and comprises holding one portion of the sheath immobile while activating an actuator which moves another portion of the sheath so that the force(s) in the sheath from the immobile portion and the moved portion force the opposing edges of a slit apart. Relieving the force(s) by returning the actuator and the moved portion of the sheath to their original locations brings the opposing edges of the slit together again to form the closed position.

As shown in FIG. 4, the sheath member is affixed on its distal end 445 to the distal end of the wand 420 and/or to the tip 460. The proximal end of the sheath is affixed to an actuator, for example, a sheath nut 430. The sheath nut 430 is rotatable, and when it rotates, it also moves the sheath 440. In the first position, with no movement by the sheath, the slit 441, is closed with its opposing edges substantially adjacent and adjoining each other. When the sheath nut 430 is rotated to a second position, the sheath 440 moves and the opposing edges of the slit 441 move apart from each other, exposing the edges and expanding the diameter of the sheath in the area of the slit, as described above. The sheath nut 430 may be held in the second position by a locking member 480, which may be a screw element that is turned to engage the proximal end of the sheath nut 430 (not shown).

In an aspect, the locking member 480 may be a sliding element that may be moved in a longitudinal direction along the longitudinal axis of handle 410 to engage the proximal end of the actuator so as to hold the actuator in the second position. In an aspect, the actuator (sheath nut 430) may be held in position 1 by locking member 480 that is a spring-loaded element such that when the locking mechanism is activated by pushing on the surface, an engaging element is released and the actuator is moved by the force of the release of the spring in a longitudinal direction along the axis of the wand or is rotated circumferentially around the wand to position 2. The actuator may be returned to position 1 by manual manipulation and reengaging the engaging element. In an aspect, the actuator may be held in position 2, after manual movement of actuator from position 1 to position 2, by activating a spring-loaded locking mechanism 480 that engages with the actuator in position 2. The actuator may be returned to position 1 by any method, for example, by manual manipulation. Position 2 may be one or more locations that are distally removed from position 1. Position 2 may be a defined distal location or may be any distally removed location chosen by the operator of the device. When position 2 is a defined distal location, the extent of the movement of the opposing edges away from each other is the same extent, and the opposing edges are moved apart to the same distance. When position 2 is an optionally chosen distally removed distance from position 1, undefined by any particular structural stopping element, the extent of the distance between the opposing edges of slit 441 is also an optional distance. Having an optionally distally removed distance location for position 2 allows for the opposing edges to be moved apart in a continuous range, from the maximum distance apart to a position of almost closed, allowing for control of the amount of expansion of the sheath member in the area of the slit 441. Once the actuator is in position 2, the position 2 location of the actuator is maintained by engaging a locking member to hold the actuator stationary, and, for example, the tissue sampling element is then used to obtain a sample that is contained within the sample collection cavity.

In an aspect, such as shown in FIG. 7, an actuator may rotate a gear or set of gears. One example of such a device, which may or may not place the sheath member under strain, is to have the actuator rotate a gear or set of gears which would transfer the longitudinal motion of an actuator into a rotational motion via a toothed ring attached to the proximal end of the sheath. FIG. 7 shows handle 710 comprising a gear system 712 which comprises a gear that is moved by action of the actuator to move the gears and affect the sheath member 740 which is affixed to the gear system 712. Actuator movement moves the gears from position 1 where the slit 741 is closed and the sample collection cavity 750 is closed, to position 2 (not shown) which opens the slit exposing the opposing edges to form the tissue sampling element and opens the sample collection cavity. An indicator 780 may be in place on the sheath member 740 or the wand 720. An atraumatic tip 760 may be on the distal end of the wand. The sheath member 740 is affixed proximate to the tip 760. The proximal end of the wand 720 is affixed to the handle 710. After a tissue sample is acquired and resident in the sample collection cavity, the actuator is moved so that the gears return to position 1, the slit closes so that the opposing edges are substantially adjacent to one another, the sample collection cavity is closed.

In an aspect, (not shown) an actuator may be moved in a longitudinal direction, in a proximal to distal direction, to move the sheath 440 so that the opposing edges of slit 441 are moved apart from each other. An actuator is moved from its most proximal site, position 1, where the slit is closed with its opposing edges substantially adjacent to each other, and the sheath member 440 is not under strain, to a second position, position 2 which is distally removed from position 1. When in position 2, the movement of sheath member 440 moves the opposing edges of the slit 441 apart so that the tissue sampling element is formed, as described herein. The actuator may be held in position 2 by a locking member 480, which may be a screw element, a sliding element or other such elements known to those skilled in the art that may interact with the actuator, the wand, the sheath member, and/or the handle 410 to maintain the actuator in position 2 and maintain the slit in an open configuration with its opposing edges apart from each other. Position 2 may be one or more locations that are distally removed from position 1. Position 2 may a defined distal location or may be any distally removed location chosen by the operator of the device. When position 2 is a defined distal location, the extent of the movement of the opposing edges away from each other is the same extent, and the opposing edges are moved apart to the same distance. When position 2 is an optionally chosen distally removed distance from position 1, undefined by any particular structural stopping element, the extent of the distance between the opposing edges of slit 441 is also an optional distance. Having an optionally distally removed distance location for position 2 allows for the opposing edges to be moved apart in a continuous range, from the maximum distance apart to a position of almost closed, allowing for control of the amount of expansion of the sheath member in the area of the slit 441. Once the actuator is in position 2, the position 2 location of the actuator is maintained by engaging a locking member to hold the actuator stationary, and, for example, the tissue sampling element is then used to obtain a sample that is contained within the sample collection cavity.

Looking at FIGS. 8 and 9, wherein like numbers indicate similarity with those of other figures, a device of the present invention comprises a tissue sampling apparatus 800, comprising, a handle 810 having a distal end 811 and a longitudinal axis, an elongated wand 820 extending outwardly from the distal end 811 of the handle 810 substantially along the longitudinal axis, wherein the wand 820 has an exterior surface, a front end 821 and a back end 822, and wherein the back end 822 is fixedly mounted to the distal end 811 of the handle 810; an actuator member 830 rotatively coupled to the distal end 811 of the handle 810, the actuator member 830 defining an opening at a first end 831 (similar to 131 of FIG. 1) that is sized to rotatively receive a portion of the wand (not shown); a sheath member 840 selectively encapsulating a portion of the wand 820 and fixedly mounted to a portion of the wand proximate to the front end 821 of the wand and to a portion of the first end 831 (similar to 131 of FIG. 1) of the actuator member 830, wherein the sheath member 840 defines a slit 841 on a distal end portion of the sheath member 840, the slit 841 being bordered by opposing edges 842 and 843, (see FIGS. 8C and 9C) wherein the distal end portion of the sheath member 840 and a portion of the exterior surface of the wand underlying the distal end portion of the sheath member define a sample collection cavity 850. As shown in FIGS. 8B and 9B, the slit 841 is selectively movable (expandable) between a closed position, (FIGS. 8B and 9B) in which the opposing edges 842 and 843 of the slit 841 substantially adjoin to substantially seal the sample collection cavity 850, and an open position, (expanded) (FIGS. 8C and 9C) in which the opposing edges 842 and 843 of the slit 841 are spaced from each other for obtaining a tissue sample when positioned within a uterine cavity by contacting the surface of the endometrial lining. When spaced apart from each other, the opposing edges 842 and 843 form a tissue sampling element such that when contacting a soft tissue surface is capable of removing tissue from a soft tissue surface, such as the inner surface of the uterine cavity. As shown in 8C and 9C, the sampling area 851 comprises an open sample collection cavity 850 with opposing edges 842 and 843 forming the tissue sampling element 846. As shown in FIGS. 8 and 9, spaced from the proximal end of the sample collection cavity 850 is an indicator 980, which may be used as a depth indicator to a user to indicate the length of the apparatus inserted into the patient and approximate location of the sample collection cavity 850. A depth stop may be placed anywhere along the shaft to provide an indication of the depth of insertion of the device.

In an aspect, (not shown), suction can be incorporated into the device to enhance collection down the proximal end of the wand 820 and/or for removal of the sample collected from the device. Reversing the suction, for example for dispensing the sample from the sample collection cavity, is also contemplated by the present invention.

The sheath may be made from a material that forms a tube covering, a sheath, having a thin wall that retains its shape. Suitable materials include but are not limited to, general classes of plastics, PTFE, PEEK, polycarbonate, nylon, polypropylene, FEP, LDPE, Topas, and other such plastics. The sheath material may also be constructed from surgical grade metals or alloys, such as stainless steel and Nitinol. The sheath material may also be fashioned from thermoset plastics such as epoxies. For example, qualities such as rigidity and transparency provide aspects desired in a sheath. Additionally, a sheath having a thin wall that is rigid allows for the formation of opposing edges of the slit that aid in scraping tissue during use. The wall of a sheath may be from about 0.100 inches to about 0.001 inches, from about 0.001 inches to about 0.050 inches, from about 0.001 inches to about 0.030 inches, from about 0.010 inches to about 0.100 inches, from about 0.010 inches to about 0.020 inches, from about 0.001 inches to about 0.010 inches, from about 0.001 inches to about 0.005 inches, from about 0.050 inches to about 0.100 inches, and widths there inbetween.

The sample collection cavity is a contained space that cannot be accessed except when the slit is in an open position. Containing a sample within the closed sample collection cavity or having the cavity itself protected by being closed protects from contamination by the presence other types of cells and prevents sample disruption or tissue loss, such as during insertion or removal of the endometrial sampling apparatus into or from the patient.

A slit may comprise one or more revolutions or rounds around the longitudinal axis of the sheath. For example, one revolution to ten revolutions may be made in a sheath, with consideration of the rigidity of the material and ability of the edges of the slit to provide an adequate scraping to obtain a sample. The number of revolutions of the slit around the longitudinal axis may affect the number of rotations of the sample collection cavity and the choice of direction, whether in one direction or both clockwise and counterclockwise, used and may be determined by the sample to be collected. One skilled in the art can determine, without undue experimentation, if an adequate sample is collected by a device of the present invention having a slit with a particular number of revolutions, and rotation number and direction.

A slit may comprise one or more slits, each having opposing edges. In an aspect, such as shown in FIG. 5, four parallel slits are present in the distal end of a sheath of a device of the present invention, with two parallel slits shown, slit 541 and slit 542. The present invention contemplates devices having one or more slits. Such slits may be shaped as helical slits, longitudinal slits or perpendicular slits, or combinations of any of these. A longitudinal slit parallels the longitudinal axis of the wand. A perpendicular slit is a slit cut perpendicular to the longitudinal axis of the wand, and may comprise a slit that extends in a radial direction around a portion of the circumference of the sheath member. Additional slit design comprises a plurality of slits, for example, with four slits parallel to the longitudinal axis of the wand, and a small slit connected to and perpendicular to each long slit. The small slit can be anywhere along the long slit, and the small slit may provide a different shape to the tissue sampling element, i.e. the small slit location can change the bend location of the exposed opposing edges when the sheath is moved to the open position.

An exemplary device is shown in FIG. 5 comprising a handle 510, a sheath member 540, an actuator 530, a wand 520, and a locking member 515. When sheath member 540 is moved in a longitudinal direction from a proximal position 1 to a distally removed position 2, the opposing edges of the parallel slits 541 and 542 are moved apart from each other, such movement also occurs with the other slits as shown in FIG. 5, slit 542 is bounded by area 545 and 546. When the opposing edges of slit 542 are moved apart, opposing edge 542a forms one border of area 545 and opposing edge 542b forms one border of area 546. The opposing edges 542a and 542b are capable of removing tissue when contacting a soft tissue surface. Slit 541 is bounded by area 545 and area 547. When opposing edges of slit 541 are moved apart, opposing edge 541a forms one border of area 545 and opposing edge 541b forms one border of area 547 (not shown). The opposing edges 541a and 541b are capable of removing tissue when contacting a soft tissue surface. The tissue sampling element formed by the movement of the opposing edges of the slits apart from each other may be used to collect a sample, and the sample is contained within the sample collection cavity formed by the reduced diameter of the wand and sheath member overlying the area where the slits are located. Simultaneously, the slits 543 and 544 (not shown) are acted on to move apart so that each slit's opposing edges to form additional opposing edges for collecting a sample.

In FIG. 5, a closed position 500 of the slits is shown and the actuator is in position 1, with no movement forces on the sheath member 540. The actuator 530 is moved to position 2 which moves the sheath member so that the opposing edges of each slit are moved apart from each other, shown as the open position 501. The actuator is moved from position 2 to position 1 to return the slits 541, 542, 543 and 544 to a closed position 500.

In use of a device of the present invention, the distal end of the device is inserted into the cervical canal and then into the uterine cavity, optionally using the tip, such as an atraumatic tip, to dilate the cervical os to some extent, so that the sampling area comprising a sample collection cavity is able to pass through the cervical canal and position in the desired location in the uterine cavity. The distance of insertion of the device may be confirmed by tactile feel by the healthcare provider or by utilizing a uterine sound. An indicator located on the sheath or wand, or a depth stop, which is a physical stop for the operator can be incorporated to assist in depth placement into the uterine cavity. For example, a depth stop may be positioned, such as slidably moved into position, at the indicator location.

Once the sampling area of the a device is in the desired location, the actuator is moved from position 1 to position 2 so as to move the sheath which causes the opposing edges of the slits present in the sheath to move apart from each other. The actuator may be maintained in position 2 by mechanisms and components described herein. The expansion of the sheath diameter at the slit(s) location allows for the opposing edges to broadly contact the inner lining of the uterine cavity without the need to move the entire device. Exposing each of the opposing edges by their movement apart from each other forms the tissue sampling element of the device. The exposed opposing edges are moved in a direction, either longitudinally along the longitudinal axis of the device, or distally and proximally from the original location, or circumferentially around the interior of the uterine cavity, or both, or multiple movements in both forward and reverse directions, and tissue from the soft tissue surface of the uterine cavity is removed and collected in the sample collection cavity. When sample collecting is complete, the actuator is moved from position 2 to position 1, and the opposing edges of the slits present in the sheath are moved together to adjoin so as to substantially close the sample collection cavity. The device is withdrawn from the patient. The sample is then removed from the sample collection cavity by moving the actuator from position 1 to position 2, thus opening the sample collection cavity by moving the opposing edges of the slit apart from each other, and the tissue contained within the sample collection cavity is removed by known methods. For example, the distal end of the device, comprising the sample collection cavity, may be placed in a container containing a histological fluid. The actuator is moved from position 1 to position 2 to move apart the opposing edges of the slit to expose the sample collection cavity and the tissue therein to be exposed to the histological fluid. The distal end of the device may be moved so as to wash the tissue from the sample collection cavity. The device may then be sterilized or discarded.

A slit may be cut into a sheath using any known cutting means, for example, by laser cutting. The cut made into the sheath for a slit may be perpendicular to the surface of the sheath and the longitudinal axis of the sheath, so that the opposing edges of the slit are oriented substantially parallel to each other and substantially normal to the exterior surface of the sheath when the slit if closed. The cut made into the sheath for a slit may be at a face angle to the surface of the sheath, so that the opposing edges of the slit are oriented substantially parallel to each other and positioned at a face angle relative to the exterior surface of the sheath when the slit if closed. When the slit is in an open position, at least a portion of one of the opposing edges of the slit are oriented at an acute angle to the longitudinal axis. Cutting a slit with edges at a face angle to the surface of the sheath may provide a slit having sharper cutting edges. Cutting a slit with edges that are saw toothed is also contemplated by the present invention. A slit having toothed opposing edges would provide a closed sample collection cavity by interleaving the teeth of each edge. The kerf or width of the cut to make the slit in the sheath should be minimized so that the sample collection cavity is adequately closed to prevent contamination or sample disruption. Cutting a slit removes material and the more material lost, as in making the kerf or width of the cut wider or larger, the less tightly the sample collection cavity will close.

The wand of the endometrial sampling apparatus may be made from any material that provides the desired characteristics, for example, rigidity and/or flexibility. Suitable materials include, but are not limited to, plastics, nylon, PEEK, stainless steel, surgical steels, Ultem, Torlon, PPS, Grivory, carbon fiber, graphite, and glass-filled Delrin, metals, any thermoplastic or thermoset material, including compositions that incorporate fillers or fibers to enhance sufficient rigidity. Considerations in choosing a material for a wand of a device of the present invention include high flexural modulus and sufficiently high rigidity, especially for the reduced diameter section of the wand. The reduced diameter section of the wand may have a diameter from about 0.100 inches to about 0.001 inches, from about 0.001 inches to about 0.050 inches, from about 0.020 inches to about 0.070 inches, from about 0.010 inches to about 0.100 inches, from about 0.010 inches to about 0.060 inches, from about 0.001 inches to about 0.080 inches, from about 0.050 inches to about 0.80 inches, from about 0.050 inches to about 0.100 inches, and widths inbetween. For example, the flexural modulus of Grivory is 2,680,000 psi, for unfilled polycarbonate is 375,000 psi, and 600,000 psi for unfilled PEEK.

A device of the present invention may have a wand of a particular diameter of the portion of the wand that does not form the sample collection cavity, which has a reduced diameter. The diameter may range from 0.050 inches to 1.0 inches, from about 0.100 inches to about 0.200, from about 0.120 inches to about 0.300 inches, from about 0.130 inches to about 0.200 inches, from about 0.140 inches to about 0.200 inches, from about 0.160 inches to about 0.200 inches, from about 0.100 inches to about 0.500 inches, from about 0.100 inches to about 0.700 inches, from about 0.050 inches to about 0.200 inches, and all diameters therein between. The length of a device of the present invention may be any desired length from the tip of the atraumatic tip to the proximal end of the handle. For example, the device may be from about 5 inches to about 25 inches, or from about 7 inches to about 15 inches, or from about 12 inches to about 15 inches, or from about 12 inches to about inches, from about 5 inches to about 15 inches, and all lengths therein between.

The length of the insertion depth into the uterine cavity, as measured from the fundus to the cervical os, may be any desired and functional length, for example from about 1 to 4 cm, from 2 to 6 cm, or from about 5 to 12 cm, and all lengths therein between. The length of the area formed by the slit for total scraping length may be any desired length that provides an adequate and complete sample of the target area, and may be, for example, from about inches to about 2.5 inches, from about 0.75 inches to about 2 inch, or from about 1 inch to 4 inches, and all lengths therein in between.

The indicator can be a marker band present on the distal end of the endometrial sampling apparatus and may be on the wand, the sheath or both or a separate depth stop set to the uterine length. Such an indicator could be a marker band added to the wand or sheath by any means known, such as by pad printing on the wand or laser etching directly on the sheath. Alternatively, a material in a contrasting color to the wand or sheath may be applied to the wand or sheath, such as by heating the contrasting colored material to the surface or to an indentation in the surface of the wand, the sheath or both. The indicator may be of any width, such as from 0.05 inches to about 1.0 inches, that is of sufficient length to be viewed during use. The indicator is placed at a predetermined distance from the proximal end of the slit, and such distance may be from about 0.05 to about 6 inches from that end or set by the user once uterine length is determined. In use, the endometrial sampling apparatus is placed into the patient to a depth where the distal end of the device touches the fundus or to a set length as pre-determined by uterine sound. The indicator is set just within the patient at the external cervical os or to a slideable depth stop set by the user, or an affixed depth stop is contacting the subject.

The sample collection cavity may have any volume desired that can be achieved by the volume of the space created by a reduced diameter wand portion and the overlaying sheath. As the diameter of a endometrial sampling apparatus may be variable, for example to accommodate differing diameters of the uterine cavity, the diameter of a opened sheath member, as measured at the extent of the opposed edges in an open position, may range from 0.05 inches to 1.0 inches, or from about 0.01 inches to about 0.75 inches, or from about 0.2 inches to about 0.5 inches, or from about 0.1 inches to about 0.3 inches, from about 0.05 inches to about 0.25 inches, and all diameters therein between. The sample collection cavity volume may differ also, and may range from 0.02 mL to about 1.2 mL. For example, the approximate volume of a sample collection cavity in a 9 FR device is 0.06 mL, the approximate volume of a sample collection cavity in a 11 Fr device is 0.12 mL and the approximate volume of a sample collection cavity in a 13 Fr Device is 0.19 mL. A diameter of an opened sheath member, as measured at the extent of the opposed edges in an open position, may be 0.223 inches. A diameter of an opened sheath member, as measured at the extent of the opposed edges in an open position, may be 0.249 inches. A diameter of an opened sheath member, as measured at the extent of the opposed edges in an open position, may be 0.288 inches. The sample collection cavity may be extended beyond the sample collection cavity to allow for capture of additional tissue. Incorporation of suction or other negative pressure means will allow the tissue sample to travel down the wand.

In an aspect, the slit may be two separate slits, each of which is substantially parallel to the longitudinal axis of the device, and each is comprised of two opposing edges. When the actuator is moved from a first position to a second position, the opposing edges are separated from each other to provide an edge to be used for scraping and to open the sample collection cavity. The device functions in the manner and for the uses described herein.

METHODS OF THE PRESENT INVENTION

A method of the present invention comprises using a device disclosed herein, such as one exemplified in FIGS. 1, 2, 3 A and 3B, 8A-C and 9A-C, and in FIGS. 4, 5, and 7 to obtain a sample comprising tissue and cells. As used herein, a sample may comprise tissue and cells, including intracellular matrix, and cellular and extracellular matter found when scraping or cutting an area of a human or animal, and may be referred to as tissue, cells or both.

A method of the present invention comprises obtaining a tissue sample, comprising providing a sampling device comprising a selectably movable sheath having at least one slit comprising opposing edges, wherein moving the sheath moves apart the opposing edges of the slit; placing the slit adjacent to a soft tissue site, moving the sheath so as to move the opposing edges of the slit apart from one another, collecting a sample by contacting the soft tissue with the opposing edges; moving the sheath so as to move the opposing edges of the slit adjacent to each other and substantially adjoining the edges; and removing the slit from the soft tissue site. The movable sheath overlays a portion of a wand. The selectably movable sheath comprises one or more slits, may comprise two slits, may comprise three slits, may comprise four slits, may comprise five slits, may comprise six slits, may comprise seven slits, may comprise ten or more slits. Moving an actuator affixed to the sheath moves the sheath. A device may comprise a wand, a moveable sheath, an actuator and a sample collection cavity. The sheath may be affixed to a distal portion of a wand (proximate to a front end) or a tip positioned on a distal end of the wand, and the sheath may be affixed to an actuator, or a component that is moved by an actuator.

A method of the present invention comprises a method of obtaining endometrial samples, comprising, providing a endometrial sampling apparatus 100, as shown in FIGS. 1, 2A and B, 3 A and B, and 6. The method comprises providing a endometrial sample apparatus comprising, a handle 110 having a distal end 111 and a longitudinal axis; an elongate wand 120 extending outwardly from the distal end 111 of the handle 110 substantially along the longitudinal axis, wherein the wand 120 has an exterior surface, a front end 121 and a back end 122, and wherein the back end 122 is fixedly mounted to the distal end 111 of the handle 110; an actuator member 130 rotatively coupled to the distal end 111 of the handle 110, the actuator member 130 defining an opening at a first end 131 that is sized to rotatively receive a portion of the wand 120; a sheath member 140 selectively encapsulating a portion of the wand 120 and fixedly mounted to a portion of the wand proximate the front end of the wand and to a portion of the first end of the actuator member, wherein the distal end portion of the sheath member and a portion of the exterior surface of the wand underlying the distal end portion of the sheath member define a sample collection cavity 150, wherein the sheath member 140 defines a helical slit 141 on a distal end portion of the sheath member, the helical slit 141 being bordered by opposing edges 142 and 143, wherein the helical slit 141 is selectively movable between a closed position 200, in which the opposing edges 142 and 143 of the helical slit substantially adjoin to substantially seal the sample collection cavity 150, and an open position 201, in which the opposing edges of the helical slit are spaced from each other; and wherein the actuator member 130 is selectively rotatable about the distal end 111 of the handle 110 between a first position 360, in which the helical slit 141 is positioned in the closed position 200, and a second position 361, in which the helical slit 141 is positioned in the open position 201; introducing and advancing the distal end portion of the sheath member to a desired location through the vaginal cavity, through the cervical canal and into the uterine cavity; rotating the actuator member to the second position 361 to selectively extend the helical slit 141 to the open position 200; selectively urging the distal end portion of the sheath member having opposing edges, wherein the opposing edges are urged against tissue at the desired location in the uterine cavity while simultaneously rotating the handle 110 of the endometrial sampling apparatus 100 to affect corresponding rotation of the open positioned helical slit to collect tissue into the sample collection cavity 150.

In an aspect, once the slit is positioned at a soft tissue site, to collect a sample, a endometrial sampling apparatus with the slit in the open position may be rotated 360 degrees one or more times in one direction, such as clockwise. In an aspect, to collect a sample, a endometrial sampling apparatus with the slit in the open position may be rotated 360 degrees one or more times in one direction, such as clockwise, followed by rotating the endometrial sampling apparatus with the slit in the open position 360 degrees one or more times in the other direction, such as counterclockwise. In an aspect, to collect a sample, a endometrial sampling apparatus with the slit in the open position may be rotated 360 degrees one time in one direction, such as clockwise, followed by rotating the endometrial sampling apparatus with the slit in the open position 360 degrees one time in the other direction, such as counterclockwise. The number of rotations made in any one direction, and the direction of rotation, in one or both directions, may be variable, depending on the user and the sample desired. A method may comprise a step of collecting a sample, comprising rotating the handle of a endometrial sampling apparatus which includes rotating the handle at least one, two, three, four, five, six, seven, eight, nine, ten or more complete revolutions, while the slit is in the open position, in one or both clockwise and counterclockwise. A benefit of the present invention is the ability to take a sample broadly from the surface contacted by the device in an open position in a 360 degree rotation of the sample collection cavity. In an aspect, a portion of the handle, and not the entire handle, may be rotated so as to rotate and urge the tissue sampling element against the tissue surface. For example, a knob portion of the handle, in a distal or proximal portion of the handle, could be rotated so as to move the wand, sheath and sampling area comprising the tissue sampling element of the device along and/or against the tissue surface to collect cells and tissue.

In an aspect, in a method of collecting a sample, once the slit is positioned at a soft tissue site, to collect a sample, a endometrial sampling apparatus with the slit in the open position may be moved in a longitudinal direction along the longitudinal axis of a endometrial sampling apparatus, from a proximal location to a distal location along one or more longitudinal lines, one or more times. A method of collecting a sample may comprise moving the slit, which is in the open position wherein the opposing edges of the slit are moved apart from each other, by moving the endometrial sampling apparatus in a longitudinal direction and in a circumferential direction, or one or both directions one or more times. Further the movement of the apparatus may be made so that a movement in a longitudinal direction comprises moving from site A in a distal direction to site B and returning from site B to site A by moving in a proximal direction. Further, the movement of the apparatus may be made so that a movement in a circumferential direction comprises moving from site A in a clockwise direction to site B or in a complete 360 degree rotation to site A again, and moving from site A in a counterclockwise direction to site B or in a complete 360 degree rotation to site A again. In an aspect, a method further comprises rotating the actuator member to the first position 360 to selectively move the helical slit 141 to the closed position 200 to selectively close the sample collection cavity 150; and withdrawing the endometrial sampling apparatus 100 from the vaginal cavity. In an aspect, the method may comprise selecting an endometrial sampling apparatus having a wand plus sheath diameter that is appropriately sized for the patient on whom the apparatus is to be used. For example, for cervical anatomy having a small diameter, an endometrial sampling apparatus having a diameter of from about 0.0.03 inches to about 3 inches may be used, and for cervical anatomy having a larger diameter, a endometrial sampling apparatus having a diameter of from about from about 0.05 inches to about 5 inches or from about 0.1 inches to about 6 inches may be used. Apparatuses of the present invention may be provided in a range of wand plus sheath diameters, wherein the diameter is measured at an area where a slit is not located, of from about 0.03 inches to about 6 inches, and all diameters thereinbetween. For example, a wand plus sheath diameter, wherein the diameter is measured at an area where a slit is not located, is approximately 0.118 inches. For example, a wand plus sheath diameter, wherein the diameter is measured at an area where a slit is not located, is approximately 0.145 inches. For example, a wand plus sheath diameter, wherein the diameter is measured at an area where a slit is not located, is approximately 0.170 inches. For example, a wand plus sheath diameter, wherein the diameter is measured at an area where a slit is not located, is approximately 0.200 inches.

In an aspect, the method may comprise selecting an endometrial sampling apparatus having a sample collection area length that is appropriately sized for the patient on whom the apparatus is to be used. For example, for uterine anatomy having a small fundus to cervical os length, an endometrial sampling apparatus having a length of from about 0.025 inches to about 1.25 inches may be used, and for uterine anatomy having a longer fundus to cervical os length, an endometrial sampling apparatus having a length of from about from about 0.05 inches to about 3 inches or from about 0.1 inches to about 5 inches may be used. Apparatuses of the present invention may be provided in a range of sample collection area lengths, wherein the length is measured at an area where a slit is located, of from about 0.03 inches to about 6 inches, and all lengths thereinbetween.

A method of the present invention comprises use of a device as shown in FIG. 4. A method comprises inserting into the uterine cavity of a female subject a device comprising a handle 410 having a longitudinal axis, an actuator 430 in a first position, a flexible wand 420, a sheath member 440 overlying the flexible wand 420, wherein the sheath member comprises at least one slit 441 and is affixed proximate to the distal end of the wand and is affixed to the actuator, and a sampling area comprising the at least one slit and a sample collection cavity wherein the device is inserted to the extent that the sampling area 415 is within the uterine cavity; moving the actuator from a first position to a second position so as to move the opposing edges of the slit away from one another to form a tissue sampling element; optionally maintaining the actuator in a second position by moving a locking member; contacting the inner surface of the uterine cavity with the tissue sampling element by moving the entire device in a circumferential direction or in a longitudinal direction along the longitudinal axis of the device, or both to obtain a sample; containing the sample in the sample collection cavity; moving the actuator to the first position so as to move the opposing edges of the slit substantially adjacent to each other, and removing the device from the subject. The device may further comprise a tip 460, which may be an atraumatic tip or a closed tip.

An actuator may comprise a sheath nut 430. Moving the actuator comprises rotating the sheath nut. Moving the actuator also moves the sheath member 440. In a first position, with no movement by the sheath, the slit 441, is closed with its opposing edges substantially adjacent and adjoining each other. When the sheath nut 430 is rotated to a second position, the sheath 440 moves and the opposing edges of the slit 441 move apart from each other, exposing the edges, the tissue sampling element. The sheath nut 430 may be held in the second position by a locking member 480, which may be a screw element that is turned to engage the proximal end of the sheath nut 430 (not shown).

In an aspect, the locking member 480 may be a sliding element that may be moved in a longitudinal direction along the longitudinal axis of handle 410 to engage the proximal end of the actuator so as to hold the actuator in the second position. In an aspect, the actuator (sheath nut 430) may be held in a first position by locking member 480 that is a spring-loaded element such that when the locking mechanism is activated by pushing on the surface, an engaging element is released and the actuator is moved by the force of the release of the spring in a longitudinal direction along the axis of the wand or is rotated circumferentially around the wand to position 2. The actuator may be returned to position 1 by manual manipulation and reengaging the engaging element. In an aspect, the actuator may be held in position 2, after manual movement of actuator from position 1 to position 2, by activating a spring-loaded locking mechanism 480 that engages with the actuator in position 2. The actuator may be returned to position 1 by any method, for example, by manual manipulation. Position 2 may be one or more locations that are distally removed from position 1. Position 2 may a defined distal location or may be any distally removed location chosen by the operator of the device. When position 2 is a defined distal location, the extent of the movement of the opposing edges away from each other is the same extent, and the opposing edges are moved apart to the same distance. When position 2 is an optionally chosen distally removed distance from position 1, undefined by any particular structural stopping element, the extent of the distance between the opposing edges of slit 441 is also an optional distance. Having an optionally distally removed distance location for position 2 allows for the opposing edges to be moved apart in a continuous range, from the maximum distance apart to a position of almost closed, allowing for control of the amount of expansion of the sheath member in the area of the slit 441. Once the actuator is in position 2, the position 2 location of the actuator is maintained by engaging a locking member to hold the actuator stationary, and, for example, the tissue sampling element is then used to obtain a sample that is contained within the sample collection cavity.

A method of the present invention comprises use of a device comprising an actuator that moves a gear or set of gears, such as shown in FIG. 7. A method comprises providing to a female subject a device comprising an actuator in mechanical connection with a gear or set of gears that when activated, the gear or set of gears move a sheath member such that opposing edges in one or more slits cut within the sheath member are moved apart or away from each other. The device may further comprise a handle 710 comprising a gear system 712 which comprises a gear that is moved by mechanical action of the actuator to move the gears and affect the sheath member 740 which is affixed to the gear system 712. Actuator movement moves the gears from a first position where the slit 741 is closed and the sample collection cavity 750 is closed, to position 2 (not shown) which opens the slit exposing the opposing edges to form the tissue sampling element and opens the sample collection cavity. An indicator 780 may be in place on the sheath member 740 or the wand 720. An atraumatic tip 760 may be on the distal end of the wand. The sheath member 740 is affixed proximate to the tip 760. The proximal end of the wand 720 is affixed to the handle 710. After a tissue sample is acquired and resident in the sample collection cavity, the actuator is moved so that the gears return to position 1, the slit closes so that the opposing edges are substantially adjacent to one another, the sample collection cavity is closed. As used herein, the terms "a first position" and "position 1" may be used interchangeably, and similarly, the terms "a second position" and "position 2" may be used interchangeably and refer to the position of an actuator and/or the position of the opposing edges of a slit, as can be determined from a careful reading of the disclosure.

In a method, a device may be provided to a female subject comprising an actuator that moves in a longitudinal direction, in a proximal to distal direction, to move the sheath 440 so that the opposing edges of slit 441 are moved apart from each other. An actuator is moved from its most proximal site, position 1, where the slit is closed with its opposing edges substantially adjacent to each other, and the sheath member 440 is not under strain, to a second position, position 2 which is distally removed from position 1. When in position 2, the movement of sheath member 440 moves the opposing edges of the slit 441 apart so that the tissue sampling element is formed, as described herein. The actuator may be held in position 2 by a locking member 480, which may be a screw element, a sliding element or other such elements known to those skilled in the art that may interact with the actuator, the wand, the sheath member, and/or the handle 410 to maintain the actuator in position 2 and maintain the slit in an open configuration with its opposing edges apart from each other. Position 2 may be one or more locations that are distally removed from position 1. Position 2 may a defined distal location or may be any distally removed location chosen by the operator of the device. When position 2 is a defined distal location, the extent of the movement of the opposing edges away from each other is the same extent, and the opposing edges are moved apart to the same distance. When position 2 is an optionally chosen distally removed distance from position 1, undefined by any particular structural stopping element, the extent of the distance between the opposing edges of slit 441 is also an optional distance. Having an optionally distally removed distance location for position 2 allows for the opposing edges to be moved apart in a continuous range, from the maximum distance apart to a position of almost closed, allowing for control of the amount of expansion of the sheath member in the area of the slit 441. Once the actuator is in position 2, the position 2 location of the actuator is maintained by engaging a locking member to hold the actuator stationary, and, for example, the tissue sampling element is then used to obtain a sample that is contained within the sample collection cavity.

Disclosed herein is a method of collecting a sample from the uterine cavity of a female, comprising inserting the distal end of a device disclosed herein through the vagina and cervical canal of a female to locate a sampling area of the device within the uterine cavity; moving an actuator from a first position to a second position which opens the sample collection cavity and provides opposing edges of at least one slit; contacting the uterine cavity with the opposing edges to acquire a tissue sample; moving the actuator from a second position to a first position; and removing the device from the subject. Alternatively, the method further comprises utilizing suction or negative pressure to enhance the collection of the tissue into the device. The method further comprises removing the sample from the device by moving the actuator from a first position to a second position which opens the sample collection cavity, and removing the tissue sample within the sample collection cavity. Alternatively, the method further comprises removing the sampling area of the device by cutting off the distal end of the device or breaking the wand to release a portion of the device comprising the sampling area. Alternatively, the method further comprises removing the sample by reverse suction and blowing the sample from the sample collection area when the device is open.

A method of the present invention comprises inserting the distal end of a device disclosed herein, optionally comprising an atraumatic tip, through the vagina and through the cervical canal into the uterine cavity. The device is inserted until the indicator passes from sight as it enters the patient and insertion is stopped by the user or the device is physically stopped by a pre-set depth stop located on the outside of the sheath. The actuator is moved from a first position to a second position to move one or more slits to the open position. The entire device or portion of the device is rotated one or more times in a 360 degree motion in one or both directions, clockwise and counterclockwise, or the device is moved longitudinally in a proximal to distal and/or distal to proximal direction, while contacting the inner surfaces of the uterine cavity with the opposing edges of the open slit to obtain tissue samples from the contacted area. Once an adequate sample is collected, the actuator is moved from the second position to the first position to close the slit and to cover and substantially close the sample collection cavity now containing the collected sample. The device is then removed from the patient. The collected sample is treated for histological examination. The sample collection cavity is protected from contamination during insertion and removal of the device into and from the patient, and is open only during sampling within the uterine cavity, and afterwards for release of the collected sample from the device. The closed position of the slit shields the sample collection cavity from contamination upon entry through the endocervical canal and into the uterine cavity, and after collection of the sample, protects the collected sample against loss of sample materials, and contamination during withdrawal of the sample collection cavity of the device from the uterine cavity and vagina.

An aspect of the present invention comprises a method of collecting a sample wherein the device is inserted one time into the patient. Once the distal end of the device is inserted into the uterine cavity of the patient, the sample is collected by rotational or longitudinal movements of the distal end of the device within the uterine cavity, and then the device is withdrawn from the patient. In contrast, methods comprising use of currently available devices to obtain a sample sometimes require multiple insertions of the device into the uterine cavity. Multiple insertions increase the opportunities for contamination of the sample, or loss of the sample, and increase the discomfort and/or pain felt by the patient. Multiple insertions also increase the variability in the sample collected as it is difficult to sample from the same site on the second and further insertions.

An example of a method of the present invention comprises inserting the distal end of the endometrial sample device, optionally comprising an atraumatic tip, through the vagina and through the cervical canal into the uterine cavity. The device is inserted until the indicator passes from sight as it enters the patient and insertion is stopped by the user or physically by a pre-set depth stop located on the outside of the sheath. The actuator is rotated from the first position to the second position to move the slit to the open position. The entire device is rotated one or more times in a 360 degree motion in one or both directions, clockwise and counterclockwise, while contacting the inner surfaces of the uterine cavity with the opposing edges of the open slit to obtain tissue samples from the contacted area. Once an adequate sample is collected, the actuator is rotated from the second position to the first position to close the slit and to cover and seal shut the sample collection cavity comprising the collected sample. The device is then removed from the patient. The collected sample is treated for histological examination. The sample collection cavity is protected from contamination during insertion and removal of the device into and from the patient, and is open only during sampling within the uterine cavity, and later for release of the collected sample from the device. The closed position of the slit shields the sample collection cavity from contamination upon entry through the endocervical canal and into the uterine cavity, and after collection of the sample, protects the collected sample against loss of sample materials, and contamination during withdrawal of the sampling area of the device from the uterine cavity and vagina.

A method of the present invention may comprise dilation of the cervical os to allow insertion of a device of the present invention. Only a small amount of force should be used to insert a device through the cervical canal, and resistance may be found in nulliparous or stenotic os patients. The device is inserted to a depth where the user stops or to a pre-set depth stop set by the user on the outside of the sheath.

A method may further comprise coating at least a portion of the wand and sheath member with a surgical lubricant or an anesthetic composition or pain medication, prior to insertion of the device into a subject.

A method of the present invention comprises insertion of a endometrial sampling apparatus so that the slit is positioned in the uterine cavity of a female, which optionally the depth of the slit (which may be one or more slits) within the patient may be indicated by the indicator located on the wand or by a depth stop contacting the outside of the external cervical os of the subject, moving (e.g., rotating) the actuator member so that the slit is in an open position; rotating the handle or part of the handle connected to the sheath, and thus the entire apparatus or the sampling part of the apparatus, 360 degrees while the moved apart opposing edges of the open slit, located in the distal end of the sheath member, are adjacent to and urged against the interior surfaces of the uterine cavity, and obtaining a sample of the endometrial tissue by scraping and/or cutting action of the opposing edges of the slit against the uterine cavity interior surfaces and the endometrial tissue is removed to the sample collection cavity. The apparatus may also be moved in a longitudinal direction, proximally to distally and back. Once the one or more 360 degree rotations of the endometrial sampling apparatus is accomplished, and the sample is collected, the rotation or movement of the endometrial sampling apparatus is stopped, and the actuator member is rotated or moved from the first position to a second position so that the slit is moved from an open position to a closed position, and the sample collection cavity is closed. Once the sample collection cavity is closed, the endometrial sampling apparatus is withdrawn from the patient. To aid in prevention of contamination of the sample, the exterior of the sheath may be rinsed to remove any adhered tissue or cells. The rinsing solution should not enter the sample collection cavity, but only rinse the exterior surface of the sheath member so that cells or tissue acquired during movement of the endometrial sampling apparatus to and from the interior of the patient and the sample collected will not be contaminated by, for example, ectocervical cells or tissue.

The tissue may be removed from the sample collection cavity by moving the actuator member from the first position to a second position so that the slit is moved from the closed position 200 to an open position 201, and the sample collection cavity is open and the tissue is accessible to be removed. For example, while in a closed position, the distal end of the endometrial sampling apparatus, where the sample collection cavity is located, may be immersed in a liquid. The actuator member is then rotated from the first position 360 to a second position 361 so that the slit is moved from the closed position 200 to an open position 201, and the sample collection cavity is open and the tissue may be washed from the sample collection cavity by flowing liquid into and out of the sample collection cavity or by moving the open sample collection cavity within the liquid. The distal tip of the device where the sample collection cavity is located may be submerged into a specimen container with liquid, and with the slit in an open position, the device is swirled or agitated to dislodge the sample. Alternatively, the sample may be retrieved from the sample collection cavity by pipettes, tweezers, graspers, or other instruments, suction, or other methods known to those skilled in the art.

It is also contemplated that the device may be designed with re-usable components and components that may be removed and discarded. It is contemplated that the removable components would contain the sampling portion of the device and can be assembled or attached on-site. The device may also be designed as a complete single-use but with a detachable segment containing the sampling portion of the device that can be snapped off or otherwise separated from the rest of the device for placement into storage fluids or containers for histological processing. For example, the distal end of the wand, which comprises the reduced diameter section forming the sample collection cavity, may be detachable from the rest of the wand. Additionally, the distal end of the sheath, comprising at least the slit, may also be detachable from the rest of the sheath. For example, at a location proximate to the sample collection cavity and slit, such as a site corresponding to the site of the indicator, the wand may be crimped or have a breakable section. Once the sample is collected and the device is removed from the patient, the distal end of the sheath is cut free from the rest of the sheath, for example by scissors or a scalpel, approximately at the site of the crimped or breakable section of the wand, and force is then used to break the wand at the crimped or breakable section. The released distal end of the wand and sheath, containing the tissue sample, may then be treated in a manner to collect and preserve the tissue sample. In an aspect, the distal end of a wand comprising the reduced diameter area may be snap-fit or screwed onto a longer segment of wand so as to form a complete assembled wand structure. The longer section of the wand may or may not be attached to a handle of a device. In use, the assembled wand structure is affixed to the handle. A sheath member may be of one piece of material or may be perforated in a location to allow the removal of a portion of the sheath. In an aspect, the sheath may be detachable from the actuator. For example, detaching the entire sheath from the actuator, and detaching the distal end of the wand but leaving the wand and the sheath attached to the tip may form a portion of the device that can be used to retrieve or store the collected tissue sample. The tip may also be removable from the wand and or the sheath. In a detached distal section of the device, comprising a tip, a portion of the sheath (or the entire sheath) and a portion of the wand, removal of the tip would allow removal of the sheath portion from the reduced diameter area of the wand so that the tissue sample is easily accessed.

Methods using a device disclosed herein may be used in obtaining tissue samples for diagnosing and prognosing disease, particularly uterine cancer. A method using a device as disclosed herein may be performed to obtain cells to diagnose endometrial lesions, which may be of particular medical significance in diagnosing high grade endometrial lesions. A method using a device as disclosed herein may be performed to assess abnormal uterine bleeding or postmenopausal bleeding. A method using a device as disclosed herein may be used prior to an endometrial ablation or any uterine procedure, for chronic anovulation, or for women that are infertile. A method using a device disclosed herein may be performed when an abnormal pap result is achieved, where there are abnormal glandular cells of unknown significance. Removing tissue samples using a device of the present invention is not particularly destructive to the uterine cavity and thus sampling with such a device may be performed routinely to monitor the uterine cavity.

It must be noted that, as used in this specification and the appended claims, the singular forms "a", "an", and "the" include plural referents unless the context clearly dictates otherwise.

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention describe in detail methods, delivery systems, and compositions to occlude the fallopian tubes of human, the present invention is not limited to these embodiments. There are numerous modifications or alterations that may suggest themselves to those skilled in the art for use of the methods, delivery systems, and compositions herein for the occlusion of a variety of conduits in both human and non-human mammals.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

REFERENCES

1. Committee on Gynecologic Practice. The Role of Transvaginal Ultrasonography in the Evaluation of Postmenopausal Bleeding. ACOG Committee Opinion. August 2009.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, dimensions, etc.), but some errors and deviations should be accounted for. Unless indicated otherwise, parts are parts by weight, temperature is in ° C. or is at ambient temperature, and pressure is at or near atmospheric.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Example 1

Sheath Collecting Endometrial Sampling System

Two endometrial sampling systems were designed having two sample collection area configurations in either 2 cm or 5 cm lengths. Each collection area version contained a spiral (or helical) cut slits with varying numbers of spiral cut revolutions in the sample collection area. The spiral cut slit is shown in FIG. 2. The devices were used to collect a tissue sample in a simulated uterine cavity. This study used a gelatin tissue phantom (Vyse Ballistic gelatin (prepared at 10% gelatin in water) to mimic the uterine cavity, as the gelatin is a type and composition used to mimic human body tissue. The 10% gelatin models were prepared using the following: 500 g water, 55.6 g gelatin, 11 drops foam eater, and 7 drops cinnamon oil. The uterine cavity was created using a mold with liquid gelatin poured into a square container approximately 5"×5". After the gelatin had cooled and solidified, the gelatin block was ready for testing. To test the devices, the device tip including the collection area was inserted directly into the gelatin block as this model represents the potential space created by the uterine cavity.

Each device was constructed of an outer sheath with a spiral cut slit. The sample collecting cavity was overlaid by the sheath and closed by one of more slits. The spiral slit 141 had either 1.5, 2 or 3 complete revolutions in the 2 or 5 cm long section of the sample collection area. The distal end of the sheath was affixed to the tip 160 of the wand 120 using cyanoacrylate adhesive. The proximal end of the sheath was affixed to an actuator 130. The section beneath the sampling area (below where the slit(s) is located) has a reduced diameter to allow for the sample to be collected. The wand 120 is affixed on its proximal end to a handle 110.

Each device was inserted into a gelatin tissue phantom and evaluated for being able to remove gelatin from the simulated uterine cavity. For the spiral cut design, the device was operated by holding the wand 120 in place while moving the sheath by rotating the handle 130, which caused the opposing edges of slit 141 to move apart from each other and open the sample collecting cavity. Rotating the actuator caused the sample collecting cavity to be open by causing the opposing edges of the slit to be displaced and moved apart from contacting each other. Once in the open position, a locking mechanism 201 held the sheath open so that the sample collecting cavity remained open. Each device was then rotated in the gelatin phantom clockwise one complete revolution and then counter-clockwise one complete revolution. The actuator was then closed 200 moving the opposing edges of the slit so as to be adjacent once again and closing the sample collecting cavity. Each device was removed from the test model and the amount of gelatin collected was evaluated. The number of cut revolutions was tested, as was the length used for the sample collection area.

The following device prototypes were prepared for testing:

| Device ID | Sheath Material | Spiral or Straight Cut | Spiral Cut #Revolutions or # of Slits for Straight cut | Wand Material |
|---|---|---|---|---|
| A | PEEK | Spiral | 2 | Stainless Steel |
| B | PEEK | Spiral | 1 | Stainless Steel |
| C | Polycarbonate | Spiral | 2 | Plastic Rod |
| D | LDPE | Spiral | 2 | Plastic Rod |
| E | LDPE | Spiral | 1 | Plastic Rod |
| F | PEEK | Straight | 4 | Stainless Steel |

Each device was tested in a new uterine cavity gelatin tissue phantom and the following results were collected:

| Device ID | Closed Sheath OD (mm) | Open Sheath OD (mm) | Amount Gelatin Collected (g) (n = 1) | Comments |
|---|---|---|---|---|
| 1 | 4.3 | 7.1 | 0.231 | Visible Material present |
| 2 | 4.3 | 7.1 | 0.237 | Visible Material present |
| 3 | 4.3 | 7.5 | 0.194 | Visible Material present |
| 4 | 4.3 | 7.5 | 0.288 | Visible Material present |
| 5 | 4.3 | 5.3 | 0.165 | Visible Material present |

All devices tested in this study removed simulated tissue material (i.e. endometrium) from the simulated uterine cavity.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A method of diagnosis of uterine disease, comprising:
    a) introducing and advancing to a desired location in an uterine cavity of a subject a distal end portion of a sheath member of an endometrial sampling apparatus comprising:
        i) a handle comprising a distal end, a second portion and a longitudinal axis, the handle comprising suction components;
        ii) an elongate wand extending outwardly from the distal end of the handle along the longitudinal axis, wherein the wand has an exterior surface, a front end and a back end, and wherein the back end is fixedly mounted to the distal end of the handle;
        iii) a selectively moveable actuator member coupled to the second portion of the handle and to the sheath member;
        iv) the sheath member selectively encapsulating a portion of the wand and fixedly mounted to the wand proximate the front end of the wand and to the actuator member, wherein the sheath member defines at least one slit on a distal end portion of the sheath member, the at least one slit being bordered by opposing edges;

wherein the distal end portion of the sheath member and the exterior surface of the wand underlying the distal end portion of the sheath member define a sample collection cavity;

b) rotating the selectively moveable actuator to a position to selectively extend the at least one slit to an open position to form a tissue sampling element;

c) selectively urging the tissue sampling element against tissue in the uterine cavity while rotating the second portion of the handle of the endometrial sampling apparatus to affect corresponding rotation of the open positioned at least one slit to collect a cellular sample into the sample collection cavity, and optionally, providing suction to assist collection of the cellular sample;

d) rotating the selectively moveable actuator member to selectively move the at least one slit to a closed position to selectively close the sample collection cavity;

e) withdrawing the endometrial sampling apparatus from the subject; and f) determining from the cellular sample whether the uterine disease is present.

2. The method of claim 1, wherein step c) comprises use of suction to assist collection of the cellular sample.

3. The method of claim 1, wherein the at least one slit is a helical slit.

4. The method of claim 1, wherein the at least one slit is a perpendicular slit.

5. The method of claim 1, wherein the endometrial sampling apparatus is a single-use device or a multiple-use device.

6. The method of claim 1, wherein the endometrial sampling apparatus further comprises a depth stop.

7. The method of claim 1, wherein the front end of the wand defines an atraumatic tip.

8. The method of claim 1, wherein the method further comprises lubricating the sheath member of the endometrial sampling apparatus before step a).

9. The method of claim 1, wherein the endometrial sampling apparatus comprises a coating of lubricant on the sheath member of the endometrial sampling apparatus.

10. The method of claim 1, wherein the suction components comprise a syringe, a pump, or an internal piston.

11. The method of claim 1, wherein the method is performed to diagnosis high grade endometrial lesions.

12. The method of claim 1, wherein the method is performed to assess abnormal uterine bleeding or prior to any uterine treatment.

13. The method of claim 1, wherein the method is performed to diagnose uterine sources of undiagnosed bleeding.

14. The method of claim 1, wherein the method is performed to determine the presence of aplastic or abnormal cells.

* * * * *